(12) United States Patent
Ness et al.

(10) Patent No.: US 8,730,479 B2
(45) Date of Patent: May 20, 2014

(54) DETECTION SYSTEM FOR DROPLET-BASED ASSAYS

(75) Inventors: Kevin D. Ness, Pleasanton, CA (US); Mark A. Arbore, Los Altos, CA (US); Jerry E. Hurst, Boulder Creek, CA (US); David L. Klein, Palo Alto, CA (US); Donald A. Masquelier, Tracy, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 13/341,678

(22) Filed: Dec. 30, 2011

(65) Prior Publication Data

US 2012/0194805 A1    Aug. 2, 2012

Related U.S. Application Data

(63) Continuation of application No. PCT/US2011/030077, filed on Mar. 25, 2011.

(60) Provisional application No. 61/317,684, filed on Mar. 25, 2010.

(51) Int. Cl.
*G01N 21/00* (2006.01)

(52) U.S. Cl.
USPC .......................................... 356/436; 356/441

(58) Field of Classification Search
USPC ............ 356/243.1–243.8, 244–246, 436–442
See application file for complete search history.

(56) References Cited

U.S. PATENT DOCUMENTS

| 3,575,220 A | 4/1971 | Davis et al. |
| 4,051,025 A | 9/1977 | Ito |
| 4,201,691 A | 5/1980 | Asher et al. |
| 4,283,262 A | 8/1981 | Cormier et al. |
| 4,348,111 A | 9/1982 | Goulas et al. |
| 4,636,075 A | 1/1987 | Knollenberg |
| 4,948,961 A | 8/1990 | Hillman et al. |
| 5,055,390 A | 10/1991 | Weaver et al. |

(Continued)

FOREIGN PATENT DOCUMENTS

| EP | 1 522 582 A2 | 4/2005 |
| EP | 1 522 582 B1 | 4/2007 |

(Continued)

OTHER PUBLICATIONS

Dasgupta et al., "Light emitting diode-based detectors Absorbance, fluorescence and spectroelectrochemical measurements in a planar flow-through cell." Analytica Chimica Acta 500 (2003) 337-364.

(Continued)

*Primary Examiner* — Tara S Pajoohi Gomez
(74) *Attorney, Agent, or Firm* — Kolish Hartwell, P.C.

(57) ABSTRACT

System, including methods and apparatus, for light detection and signal processing for droplet-based assays. An exemplary system provides a method of detection for droplets. An examination region of a channel may be illuminated with first pulses of light interleaved with second pulses of light as droplets pass through the examination region, the first pulses being spectrally distinct from the second pulses. Data may be collected representing light detected during illumination of the examination region with the first pulses and the second pulses. Each droplet may be illuminated with a beam of light that is narrower than a diameter of the droplets.

22 Claims, 12 Drawing Sheets

(56) References Cited

U.S. PATENT DOCUMENTS

| | | |
|---|---|---|
| 5,176,203 A | 1/1993 | Larzul |
| 5,225,332 A | 7/1993 | Weaver et al. |
| 5,270,183 A | 12/1993 | Corbett et al. |
| 5,314,809 A | 5/1994 | Erlich et al. |
| 5,344,930 A | 9/1994 | Riess et al. |
| 5,422,277 A | 6/1995 | Connelly et al. |
| 5,538,667 A | 7/1996 | Hill et al. |
| 5,555,191 A | 9/1996 | Hripcsak |
| 5,585,069 A | 12/1996 | Zanzucchi et al. |
| 5,587,128 A | 12/1996 | Wilding et al. |
| 5,602,756 A | 2/1997 | Atwood et al. |
| 5,720,923 A | 2/1998 | Haff et al. |
| 5,736,314 A | 4/1998 | Hayes et al. |
| 5,779,977 A | 7/1998 | Haff et al. |
| 5,827,480 A | 10/1998 | Haff et al. |
| 5,856,174 A | 1/1999 | Lipshutz et al. |
| 5,912,945 A | 6/1999 | Da Silva et al. |
| 5,928,907 A | 7/1999 | Woudenberg et al. |
| 5,945,334 A | 8/1999 | Besemer et al. |
| 5,972,716 A | 10/1999 | Ragusa et al. |
| 5,980,936 A | 11/1999 | Krafft et al. |
| 5,994,056 A | 11/1999 | Higuchi |
| 6,033,880 A | 3/2000 | Haff et al. |
| 6,042,709 A | 3/2000 | Parce et al. |
| 6,057,149 A | 5/2000 | Burns et al. |
| 6,126,899 A | 10/2000 | Woudenberg et al. |
| 6,130,098 A | 10/2000 | Handique et al. |
| 6,143,496 A | 11/2000 | Brown et al. |
| 6,146,103 A | 11/2000 | Lee et al. |
| 6,171,785 B1 | 1/2001 | Higuchi |
| 6,175,669 B1 | 1/2001 | Colston et al. |
| 6,176,609 B1 | 1/2001 | Cleveland et al. |
| 6,177,479 B1 | 1/2001 | Nakajima et al. |
| 6,210,879 B1 | 4/2001 | Meloni et al. |
| 6,258,569 B1 | 7/2001 | Livak et al. |
| 6,281,254 B1 | 8/2001 | Nakajima et al. |
| 6,303,343 B1 | 10/2001 | Kopf-Sill |
| 6,357,907 B1 | 3/2002 | Cleveland et al. |
| 6,384,915 B1 | 5/2002 | Everett et al. |
| 6,391,559 B1 | 5/2002 | Brown et al. |
| 6,440,706 B1 | 8/2002 | Vogelstein et al. |
| 6,466,713 B2 | 10/2002 | Everett et al. |
| 6,488,895 B1 | 12/2002 | Kennedy |
| 6,489,103 B1 | 12/2002 | Griffiths et al. |
| 6,494,104 B2 | 12/2002 | Kawakita et al. |
| 6,509,085 B1 | 1/2003 | Kennedy |
| 6,521,427 B1 | 2/2003 | Evans |
| 6,524,456 B1 | 2/2003 | Ramsey et al. |
| 6,540,895 B1 | 4/2003 | Spence et al. |
| 6,551,841 B1 | 4/2003 | Wilding et al. |
| 6,558,916 B2 | 5/2003 | Veerapandian et al. |
| 6,575,188 B2 | 6/2003 | Parunak |
| 6,602,472 B1 | 8/2003 | Zimmermann et al. |
| 6,620,625 B2 | 9/2003 | Wolk et al. |
| 6,637,463 B1 | 10/2003 | Lei et al. |
| 6,638,749 B1 | 10/2003 | Beckman et al. |
| 6,660,367 B1 | 12/2003 | Yang et al. |
| 6,663,619 B2 | 12/2003 | Odrich et al. |
| 6,664,044 B1 | 12/2003 | Sato |
| 6,670,153 B2 | 12/2003 | Stern |
| 6,753,147 B2 | 6/2004 | Vogelstein et al. |
| 6,767,706 B2 | 7/2004 | Quake et al. |
| 6,773,566 B2 | 8/2004 | Shenderov |
| 6,808,882 B2 | 10/2004 | Griffiths et al. |
| 6,814,934 B1 | 11/2004 | Higuchi |
| 6,833,242 B2 | 12/2004 | Quake et al. |
| 6,900,021 B1 | 5/2005 | Harrison et al. |
| 6,905,885 B2 | 6/2005 | Colston et al. |
| 6,949,176 B2 | 9/2005 | Vacca et al. |
| 6,960,437 B2 | 11/2005 | Enzelberger et al. |
| 6,964,846 B1 | 11/2005 | Shuber |
| 7,010,391 B2 | 3/2006 | Handique et al. |
| 7,041,481 B2 | 5/2006 | Anderson et al. |
| 7,052,244 B2 | 5/2006 | Fouillet et al. |
| 7,081,336 B2 | 7/2006 | Bao et al. |
| 7,091,048 B2 | 8/2006 | Parce et al. |
| 7,094,379 B2 | 8/2006 | Fouillet et al. |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,141,537 B2 | 11/2006 | Audenaert et al. |
| 7,192,557 B2 | 3/2007 | Wu et al. |
| 7,198,897 B2 | 4/2007 | Wangh et al. |
| 7,238,268 B2 | 7/2007 | Ramsey et al. |
| 7,244,567 B2 | 7/2007 | Chen et al. |
| 7,252,943 B2 | 8/2007 | Griffiths et al. |
| 7,268,167 B2 | 9/2007 | Higuchi et al. |
| 7,268,179 B2 | 9/2007 | Brown |
| 7,270,786 B2 | 9/2007 | Parunak et al. |
| 7,279,146 B2 | 10/2007 | Nassef et al. |
| 7,294,468 B2 | 11/2007 | Bell et al. |
| 7,294,503 B2 | 11/2007 | Quake et al. |
| 7,306,929 B2 | 12/2007 | Ignatov et al. |
| 7,312,085 B2 | 12/2007 | Chou et al. |
| 7,323,305 B2 | 1/2008 | Leamon et al. |
| 7,368,233 B2 | 5/2008 | Shuber et al. |
| 7,375,140 B2 | 5/2008 | Higuchi et al. |
| 7,423,751 B2 * | 9/2008 | Hairston et al. ............... 356/318 |
| 7,429,467 B2 | 9/2008 | Holliger et al. |
| 7,567,596 B2 | 7/2009 | Dantus et al. |
| 7,579,172 B2 | 8/2009 | Cho et al. |
| 7,595,195 B2 | 9/2009 | Lee et al. |
| 7,622,280 B2 | 11/2009 | Holliger et al. |
| 7,629,123 B2 | 12/2009 | Millonig et al. |
| 7,776,927 B2 | 8/2010 | Chu et al. |
| 7,807,920 B2 | 10/2010 | Linke et al. |
| 7,842,457 B2 | 11/2010 | Berka et al. |
| 8,399,198 B2 | 3/2013 | Hiddessen et al. |
| 2001/0046701 A1 | 11/2001 | Schulte et al. |
| 2002/0021866 A1 | 2/2002 | Everett et al. |
| 2002/0022261 A1 | 2/2002 | Anderson et al. |
| 2002/0060156 A1 | 5/2002 | Mathies et al. |
| 2002/0068357 A1 | 6/2002 | Mathies et al. |
| 2002/0093655 A1 | 7/2002 | Everett et al. |
| 2002/0141903 A1 | 10/2002 | Parunak et al. |
| 2002/0142483 A1 | 10/2002 | Yao et al. |
| 2002/0151040 A1 | 10/2002 | O'Keefe et al. |
| 2002/0164820 A1 | 11/2002 | Brown |
| 2002/0195586 A1 | 12/2002 | Auslander et al. |
| 2003/0001121 A1 | 1/2003 | Hochstein |
| 2003/0003054 A1 | 1/2003 | McDonald et al. |
| 2003/0003441 A1 | 1/2003 | Colston et al. |
| 2003/0008308 A1 | 1/2003 | Enzelberger et al. |
| 2003/0027150 A1 | 2/2003 | Katz |
| 2003/0027244 A1 | 2/2003 | Colston et al. |
| 2003/0027352 A1 | 2/2003 | Hooper et al. |
| 2003/0032172 A1 | 2/2003 | Colston, Jr. et al. |
| 2003/0049659 A1 | 3/2003 | Lapidus et al. |
| 2003/0087300 A1 | 5/2003 | Knapp et al. |
| 2003/0170698 A1 | 9/2003 | Gascoyne et al. |
| 2003/0180765 A1 | 9/2003 | Traverso et al. |
| 2003/0204130 A1 | 10/2003 | Colston, Jr. et al. |
| 2004/0007463 A1 | 1/2004 | Ramsey et al. |
| 2004/0038385 A1 | 2/2004 | Langlois et al. |
| 2004/0067493 A1 | 4/2004 | Matsuzaki et al. |
| 2004/0068019 A1 | 4/2004 | Higuchi et al. |
| 2004/0074849 A1 | 4/2004 | Brown et al. |
| 2004/0171055 A1 | 9/2004 | Brown |
| 2004/0180346 A1 | 9/2004 | Anderson et al. |
| 2004/0208792 A1 | 10/2004 | Linton et al. |
| 2005/0036920 A1 | 2/2005 | Gilbert |
| 2005/0042639 A1 | 2/2005 | Knapp et al. |
| 2005/0064460 A1 | 3/2005 | Holliger et al. |
| 2005/0079510 A1 | 4/2005 | Berka et al. |
| 2005/0112541 A1 | 5/2005 | Durack et al. |
| 2005/0172476 A1 | 8/2005 | Stone et al. |
| 2005/0202429 A1 | 9/2005 | Trau et al. |
| 2005/0221279 A1 | 10/2005 | Carter et al. |
| 2005/0221373 A1 | 10/2005 | Enzelberger et al. |
| 2005/0227264 A1 | 10/2005 | Nobile et al. |
| 2005/0239192 A1 | 10/2005 | Nasarabadi et al. |
| 2005/0277125 A1 | 12/2005 | Benn et al. |
| 2005/0282206 A1 | 12/2005 | Corbett et al. |
| 2006/0014187 A1 | 1/2006 | Li et al. |

(56) References Cited

U.S. PATENT DOCUMENTS

| | | |
|---|---|---|
| 2006/0057599 A1 | 3/2006 | Dzenitis et al. |
| 2006/0077755 A1 | 4/2006 | Higuchi et al. |
| 2006/0079583 A1 | 4/2006 | Higuchi et al. |
| 2006/0079584 A1 | 4/2006 | Higuchi et al. |
| 2006/0079585 A1 | 4/2006 | Higuchi et al. |
| 2006/0094108 A1 | 5/2006 | Yoder et al. |
| 2006/0106208 A1 | 5/2006 | Nochumson et al. |
| 2006/0188463 A1 | 8/2006 | Kim et al. |
| 2007/0003442 A1 | 1/2007 | Link et al. |
| 2007/0010974 A1 | 1/2007 | Nicoli et al. |
| 2007/0048756 A1 | 3/2007 | Mei et al. |
| 2007/0109542 A1 | 5/2007 | Tracy et al. |
| 2007/0166200 A1 | 7/2007 | Zhou et al. |
| 2007/0195127 A1 | 8/2007 | Ahn et al. |
| 2007/0196397 A1 | 8/2007 | Torii et al. |
| 2007/0202525 A1 | 8/2007 | Quake et al. |
| 2007/0231393 A1 | 10/2007 | Ritter et al. |
| 2007/0242111 A1 | 10/2007 | Pamula et al. |
| 2007/0248956 A1 | 10/2007 | Buxbaum et al. |
| 2007/0258083 A1 | 11/2007 | Heppell et al. |
| 2008/0003142 A1 | 1/2008 | Link et al. |
| 2008/0014589 A1 | 1/2008 | Link et al. |
| 2008/0038810 A1 | 2/2008 | Pollack et al. |
| 2008/0070862 A1 | 3/2008 | Laster et al. |
| 2008/0090244 A1 | 4/2008 | Knapp et al. |
| 2008/0138815 A1 | 6/2008 | Brown et al. |
| 2008/0145923 A1 | 6/2008 | Hahn et al. |
| 2008/0153091 A1 | 6/2008 | Brown et al. |
| 2008/0160525 A1 | 7/2008 | Brown et al. |
| 2008/0161420 A1 | 7/2008 | Shuber |
| 2008/0166793 A1 | 7/2008 | Beer et al. |
| 2008/0169184 A1 | 7/2008 | Brown et al. |
| 2008/0169195 A1 | 7/2008 | Jones et al. |
| 2008/0171324 A1 | 7/2008 | Brown et al. |
| 2008/0171325 A1 | 7/2008 | Brown et al. |
| 2008/0171326 A1 | 7/2008 | Brown et al. |
| 2008/0171327 A1 | 7/2008 | Brown et al. |
| 2008/0171380 A1 | 7/2008 | Brown et al. |
| 2008/0171382 A1 | 7/2008 | Brown et al. |
| 2008/0213766 A1 | 9/2008 | Brown et al. |
| 2008/0214407 A1 | 9/2008 | Remacle et al. |
| 2008/0262384 A1 | 10/2008 | Wiederkehr et al. |
| 2008/0268436 A1 | 10/2008 | Duan et al. |
| 2008/0274455 A1 | 11/2008 | Puskas et al. |
| 2008/0280331 A1 | 11/2008 | Davies et al. |
| 2008/0280865 A1 | 11/2008 | Tobita |
| 2008/0280955 A1 | 11/2008 | McCamish |
| 2008/0314761 A1 | 12/2008 | Herminghaus et al. |
| 2009/0012187 A1 | 1/2009 | Chu et al. |
| 2009/0026082 A1 | 1/2009 | Rothberg et al. |
| 2009/0029867 A1 | 1/2009 | Reed et al. |
| 2009/0035770 A1 | 2/2009 | Mathies et al. |
| 2009/0035838 A1 | 2/2009 | Quake et al. |
| 2009/0061428 A1 | 3/2009 | McBride et al. |
| 2009/0068170 A1 | 3/2009 | Weitz et al. |
| 2009/0069194 A1 | 3/2009 | Ramakrishnan |
| 2009/0098044 A1 | 4/2009 | Kong et al. |
| 2009/0114043 A1 | 5/2009 | Cox |
| 2009/0131543 A1 | 5/2009 | Weitz et al. |
| 2009/0161108 A1* | 6/2009 | Frese et al. .................. 356/440 |
| 2009/0162929 A1 | 6/2009 | Ikeda |
| 2009/0176271 A1 | 7/2009 | Durack et al. |
| 2009/0203063 A1 | 8/2009 | Wheeler et al. |
| 2009/0217742 A1 | 9/2009 | Chiu et al. |
| 2009/0220434 A1 | 9/2009 | Sharma |
| 2009/0235990 A1 | 9/2009 | Beer |
| 2009/0239308 A1 | 9/2009 | Dube et al. |
| 2009/0291435 A1 | 11/2009 | Unger et al. |
| 2009/0311713 A1 | 12/2009 | Pollack et al. |
| 2009/0325184 A1 | 12/2009 | Woudenberg et al. |
| 2009/0325234 A1 | 12/2009 | Gregg et al. |
| 2009/0325236 A1 | 12/2009 | Griffiths et al. |
| 2010/0009360 A1 | 1/2010 | Rosell Costa et al. |
| 2010/0020565 A1 | 1/2010 | Seward |
| 2010/0022414 A1 | 1/2010 | Link et al. |
| 2010/0041046 A1 | 2/2010 | Chiu et al. |
| 2010/0047808 A1 | 2/2010 | Reed et al. |
| 2010/0069250 A1 | 3/2010 | White, III et al. |
| 2010/0069263 A1 | 3/2010 | Shendure et al. |
| 2010/0092973 A1 | 4/2010 | Davies et al. |
| 2010/0137163 A1 | 6/2010 | Link et al. |
| 2010/0173394 A1 | 7/2010 | Colston, Jr. et al. |
| 2010/0248385 A1 | 9/2010 | Tan et al. |
| 2010/0261229 A1 | 10/2010 | Lau et al. |
| 2010/0304446 A1 | 12/2010 | Davies et al. |
| 2010/0304978 A1 | 12/2010 | Deng et al. |
| 2011/0000560 A1 | 1/2011 | Miller et al. |
| 2011/0027394 A1 | 2/2011 | McCements et al. |
| 2011/0053798 A1 | 3/2011 | Hindson et al. |
| 2011/0070589 A1 | 3/2011 | Belgrader et al. |
| 2011/0086780 A1 | 4/2011 | Colston, Jr. et al. |
| 2011/0092373 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0118151 A1 | 5/2011 | Eshoo et al. |
| 2011/0160078 A1 | 6/2011 | Fodor et al. |
| 2011/0177563 A1 | 7/2011 | Hahn et al. |
| 2011/0183330 A1 | 7/2011 | Lo et al. |
| 2011/0212516 A1 | 9/2011 | Ness et al. |
| 2011/0217712 A1 | 9/2011 | Hiddessen et al. |
| 2011/0217736 A1 | 9/2011 | Hindson |
| 2011/0218123 A1 | 9/2011 | Weitz et al. |
| 2011/0244455 A1 | 10/2011 | Larson et al. |
| 2011/0250597 A1 | 10/2011 | Larson et al. |
| 2011/0311978 A1 | 12/2011 | Makarewicz, Jr. et al. |
| 2012/0021423 A1 | 1/2012 | Colston, Jr. et al. |
| 2012/0028311 A1 | 2/2012 | Colston, Jr. et al. |
| 2012/0122714 A1 | 5/2012 | Samuels et al. |
| 2012/0152369 A1 | 6/2012 | Hiddessen et al. |
| 2012/0171683 A1 | 7/2012 | Ness et al. |
| 2012/0190032 A1 | 7/2012 | Ness et al. |
| 2012/0190033 A1 | 7/2012 | Ness et al. |
| 2012/0208241 A1 | 8/2012 | Link |
| 2012/0219947 A1 | 8/2012 | Yurkovetsky et al. |
| 2012/0220494 A1 | 8/2012 | Samuels et al. |
| 2012/0264646 A1 | 10/2012 | Link et al. |
| 2012/0302448 A1 | 11/2012 | Hutchison et al. |
| 2012/0309002 A1 | 12/2012 | Link |
| 2012/0329664 A1 | 12/2012 | Saxonov et al. |
| 2013/0017551 A1 | 1/2013 | Dube |
| 2013/0040841 A1 | 2/2013 | Saxonov et al. |
| 2013/0045875 A1 | 2/2013 | Saxonov et al. |
| 2013/0059754 A1 | 3/2013 | Tzonev |
| 2013/0064776 A1 | 3/2013 | El Harrak et al. |
| 2013/0084572 A1 | 4/2013 | Hindson et al. |
| 2013/0099018 A1 | 4/2013 | Miller et al. |
| 2013/0109575 A1 | 5/2013 | Kleinschmidt et al. |

FOREIGN PATENT DOCUMENTS

| | | |
|---|---|---|
| GB | 1 503 163 | 3/1978 |
| GB | 2 097 692 | 11/1982 |
| JP | 0295433 | 4/1990 |
| WO | 82/02562 | 8/1982 |
| WO | 84/02000 | 5/1984 |
| WO | 92/01812 | 2/1992 |
| WO | 94/05414 | 3/1994 |
| WO | 96/12194 | 4/1996 |
| WO | 98/00231 | 1/1998 |
| WO | 98/16313 | 4/1998 |
| WO | 98/44151 | 10/1998 |
| WO | 98/44152 | 10/1998 |
| WO | 98/47003 | 10/1998 |
| WO | 01/07159 | 2/2001 |
| WO | 01/12327 | 2/2001 |
| WO | 02/23163 | 3/2002 |
| WO | 02/060584 | 8/2002 |
| WO | 02/068104 | 9/2002 |
| WO | 02/081490 | 10/2002 |
| WO | 02/081729 | 10/2002 |
| WO | 03/016558 | 2/2003 |
| WO | 03/042410 | 5/2003 |
| WO | 03/072258 | 9/2003 |
| WO | 2004/040001 | 5/2004 |

(56) References Cited

FOREIGN PATENT DOCUMENTS

| | | |
|---|---|---|
| WO | 2005/007812 | 1/2005 |
| WO | 2005/010145 | 2/2005 |
| WO | 2005/021151 | 3/2005 |
| WO | 2005/023091 | 3/2005 |
| WO | 2005/055807 | 6/2005 |
| WO | 2005/073410 | 8/2005 |
| WO | 2005/075683 | 8/2005 |
| WO | 2006/023719 | 3/2006 |
| WO | 2006/027757 | 3/2006 |
| WO | 2006/038035 | 4/2006 |
| WO | 2006/086777 | 8/2006 |
| WO | 2006/095981 | 9/2006 |
| WO | 2007/091228 | 8/2007 |
| WO | 2007/091230 | 8/2007 |
| WO | 2007/092473 | 8/2007 |
| WO | 2007/133710 | 11/2007 |
| WO | 2008/021123 | 2/2008 |
| WO | 2008/024114 | 2/2008 |
| WO | 2008/063227 | 5/2008 |
| WO | 2008/070074 | 6/2008 |
| WO | 2008/070862 | 6/2008 |
| WO | 2008/109176 | 9/2008 |
| WO | 2008/109878 | 9/2008 |
| WO | 2008/112177 | 9/2008 |
| WO | 2009/002920 | 12/2008 |
| WO | 2009/015863 | 2/2009 |
| WO | 2009/049889 | 4/2009 |
| WO | 2009/085246 | 7/2009 |
| WO | 2010/001419 | 1/2010 |
| WO | 2010/018465 | 2/2010 |
| WO | 2011/034621 | 3/2011 |
| WO | 2011/079176 | 6/2011 |

OTHER PUBLICATIONS

Jin et al., "Practical Time-Gated Luminescence Flow Cytometry. II: Experimental Evaluation Using UV LED Excitation." International Society for Analytical Cytology, published online Wiley InterScience, Cytometry Part A. 71A (2007) 797-808. <http:onlinelibrary.wiley.com/doi/10.1002/cyto.a.20449/full>.

Nie and Zare, "Optical Detection of Single Moleculres." Annual Rev. Biophys. Biomol. Struct. 26 (1997) 567-96. <http://www.wfu.edu/chemistry/courses/jonesbt/334/SM2.pdf>.

Schroeder et al., "Introduction to Flow Cytometry." Version 5.1, 2004 (c) Groff M. Schroeder and Douglas E. Swartzendruber. <http://appliedtechnologyproducts.com/Send/IntroductiontoFlowCytometry5-1.pdf>.

Young, Lee W., Authorized officer. International Searching Authority, International Search Report, International Application Serial No. PCT/US2011/030077; search completion: Jul. 2, 2011; mail date: Jul. 18, 2011.

Young, Lee W., Authorized officer. International Searching Authority, Written Opinion of the International Searching Authority, International Application Serial No. PCT/US2011/030077; opinion completion: Jul. 3, 2011; mail date: Jul. 18, 2011.

J. Smid-Korbar et al., "Efficiency and usability of silicone surfactants in emulsions," International Journal of Cosmetic Science 12, pp. 135-139, (1990), presented at the 15th IFSCC International Congress, Sep. 26-29, 1988, London.

A. Chittofrati et al., "Perfluoropolyether microemulsions," Progress in Colloid & Polymer Science 79, pp. 218-225, (1989).

Steven A. Snow, "Synthesis and Characterization of Zwitterionic Silicone Sulfobetaine Surfactants," Langmuir, vol. 6, No. 2, American Chemical Society, pp. 385-391, (1990).

Polydimethylsiloxane, 5 pgs., published in FNP 52 (1992).

Russell Higuchi et al., "Kinetic PCR Analysis: Real-time Monitoring of DNA Amplification Reactions," Bio/Technology vol. II, pp. 1026-1030, Sep. 11, 1993.

D. A. Newman et al., "Phase Behavior of Fluoroether-Functional Amphiphiles in Supercritical Carbon Dioxide," The Journal of Supercritical Fluids, vol. 6, No. 4, pp. 205-210, (1993).

Y. Sela et al., "Newly designed polysiloxane-graft-poly (oxyethylene) copolymeric surfactants: preparation, surface activity and emulsification properties," Colloid & Polymer Science 272, pp. 684-691, (1994).

M. Gasperlin et al., "The structure elucidation of semisolid w/o emulsion systems containing silicone surfactant," International Journal of Pharmaceutics 107, pp. 51-56, (1994).

Mieczyslaw A. Piatyszek et al., "Detection of telomerase activity in human cells and tumors by a telomeric repeat amplification protocol (TRAP)," Methods in Cell Science 17, pp. 1-15, (1995).

Anthony P. Shuber et al., "A Simplified Procedure for Developing Multiplex PCRs," Genome Research, published by Cold Spring Harbor Laboratory Press, pp. 488-493, (1995).

A. V. Yazdi et al., "Highly Carbon Dioxide Soluble Surfactants, Dispersants and Chelating Agents," Fluid Phase Equilibria, vol. 117, pp. 297-303, (1996).

Ariel A. Avilion et al., "Human Telomerase RNA and Telomerase Activity in Immortal Cell Lines and Tumor Tissues," Cancer Research 56, pp. 645-650, Feb. 1, 1996.

Edith J. Singley et al., "Phase behavior and emulsion formation of novel fluoroether amphiphiles in carbon dioxide," Fluid Phase Equilibria 128, pp. 199-219, (1997).

Olga Kalinina et al., "Nanoliter scale PCR with TaqMan Detection," Nucleic Acids Research, vol. 25, No. 10 pp. 1999-2004, (1997).

Zhen Guo et al , "Enhanced discrimination of single nucleotide polymorphisms by artificial mismatch hybridization," Nature Biotechnology vol. 15, pp. 331-335, Apr. 1997.

E. G. Ghenciu et al., "Affinity Extraction into Carbon Dioxide. 1. Extraction of Avidin Using a Biotin-Functional Fluoroether Surfactant," Ind. Eng. Chem. Res. vol. 36, No. 12, pp. 5366-5370, Dec. 1, 1997.

Paschalis Alexandridis, Structural Polymorphism of Poly(ethylene oxide)-Poly(propylene oxide) Block Copolymers in Nonaqueous Polar Solvents, Macromolecules, vol. 31, No. 20, pp. 6935-6942, Sep. 12, 1998.

Sandro R. P. Da Rocha et al., "Effect of Surfactants on the Interfacial Tension and Emulsion Formation between Water and Carbon Dioxide," Langmuir, vol. 15, No. 2, pp. 419-428, (1999), published on web Dec. 29, 1998.

Bert Vogelstein et al., "Digital PCR," Proc. Natl. Acad. Sci. USA, vol. 96, pp. 9236-9241, Aug. 1999.

Anthony J. O'Lenick, Jr., "Silicone Emulsions and Surfactants," Journal of Surfactants and Detergents, vol. 3, No. 3, Jul. 2000.

N. Garti et al., "Water Solubilization in Nonionic Microemulsions Stabilized by Grafted Siliconic Emulsifiers," Journal of Colloid and Interface Science vol. 233, pp. 286-294, (2001).

Shinji Katsura et al., "Indirect micromanipulation of single molecules in water-in-oil emulsion," Electrophoresis, vol. 22, pp. 289-293, (2001).

Hironobu Kunieda et al., "Effect of Hydrophilic- and Hydrophobic-Chain Lengths on the Phase Behavior of A-B-type Silicone Surfactants in Water," J. Phys. Chem. B, vol. 105, No. 23, pp. 5419-5426, (2001).

Hidenori Nagai et al., "Development of a Microchamber Array for Picoliter PCR," Analytical Chemistry, vol. 73, No. 5, pp. 1043-1047, Mar. 1, 2001.

Christopher B. Price, "Regular Review Point of Care Testing," BMJ, vol. 322, May 26, 2001.

3M Specialty Materials, "3M Fluorinert Electronic Liquid FC-3283," product information guide, issued Aug. 2001.

Ivonne Schneegaβ et al., "Miniaturized flow-through PCR with different template types in a silicon chip thermocycler," Lab on a Chip, vol. 1, pp. 42-49, (2001).

Randla M. Hill, "Silicone surfactants—new developments," Current Opinion in Colloid & Interface Science 7, pp. 255-261, (2002).

Richard M. Cawthon, "Telomere measurement by quantitative PCR," Nucleic Acids Research, vol. 30, No. 10, pp. 1-6, (2002).

Anfeng Wang et al., "Direct Force Measurement of Silicone- and Hydrocarbon-Based ABA Triblock Surfactants in Alcoholic Media by Atomic Force Mircroscopy," Journal of Colloid and Interface Science 256, pp. 331-340 (2002).

(56) References Cited

OTHER PUBLICATIONS

Shelley L. Anna et al., "Formation of dispersions using "flow focusing" in microchannels," Applied Physics Letters, vol. 82, No. 3, Jan. 20, 2003.
Goldschmidt GMBH, "Abil® EM 90 Emulsifier for the formulation of cosmetic W/O creams and lotions," degussa. creating essentials brochure, pp. 1-7, May 2003.
R. G. Rutledge et al., "Mathematics of quantitative kinetic PCR and the application of standard curves," Nucleic Acids Research, vol. 31, No. 16, pp. 1-6, (2003).
Chunming Ding et al., "Direct molecular haplotyping of long-range genomic DNA with M1-PCR," PNAS, vol. 100, No. 13, pp. 7449-7453, Jun. 24, 2003.
Devin Dressman et al., "Transforming single DNA molecules into fluorescent magnetic particles for detection and enumeration of genetic variations," PNAS, vol. 100, No. 15, Jul. 22, 2003.
Ulf Landegren et al., "Padlock and proximity probes for in situ and array-based analyses: tools for the post-genomic era," Comp. Funct. Genom, vol. 4, pp. 525-530, (2003).
Gudrun Pohl et al., "Principle and applications of digital PCR" review, www.future-drugs.com, Expert Rev. Mol. Diagn. 4(1), pp. 41-47, (2004).
Stéphane Swillens et al., "Instant evaluation of the absolute initial Number of cDNA copies from a single real-time PCR curve," Nucleic Acids Research, vol. 32, No. 6, pp. 1-6, (2004).
Mats Gullberg et al., "Cytokine detection by antibody-based proximity ligation," PNAS, vol. 101, No. 22, pp. 8420-8424, Jun. 1, 2004.
Tianhao Zhang et al., "Behavioral Modeling and Performance Evaluation of Microelectrofluidics-Based PCR Systems Using SystemC," IEEE Transactions on Computer-Aided Design of Integrated Circuits and Systems, vol. 23, No. 6, pp. 843-858, Jun. 2004.
R. G. Rutledge, "Sigmoidal curve-fitting redefines quantitative real-time PCR with the prospective of developing automated high-throughput applications," Nucleic Acids Research. vol. 32, No. 22, pp. 1-8, (2004).
L. Spencer Roach et al., "Controlling Nonspecific Protein Absorption in a Plug-Based Microfluidic System by Controlling Interfacial Chemistry Using Fluorous-Phase Surfactants," Analytical Chemistry vol. 77, No. 3, pp. 785-796, Feb. 1, 2005.
Kevin D. Dorfman et al., "Contamination-Free Continuous Flow Microfluidic Polymerase Chain Reaction for Quantitative and Clinical Applications," Analytical Chemistry vol. 77, No. 11, pp. 3700-3704, Jun. 1, 2005.
James G. Wetmur et al., "Molecular haplotyping by linking emulsion PCR: analysis of paraoxonase 1 haplotypes and phenotypes," Nucleic Acids Research, vol. 33, No. 8, pp. 2615-2619, (2005).
Piotr Garstecki et al., "Mechanism for Flow-Rate Controlled Breakup in Confined Geometries: A Route to Monodisperse Emulsions," Physical Review Letters, 164501, pp. 164501-1-164501-4, Apr. 29, 2005.
Anna Musyanovych et al., "Miniemulsion Droplets as Single Molecule Nanoreactors for Polymerase Chain Reaction," Biomacromolecules, vol. 6, No. 4, pp. 1824-1828, (2005).
Max Chabert et al., "Droplet fusion by alternating current (AC) field electrocoalescence in microchannels," Electrophoresis, vol. 26, pp. 3706-3715, (2005).
Takaaki Kojima et al., "PCR amplification from single DNA molecules on magnetic beads in emulsion: application for high-throughput screening of transcription factor targets," Nucleic Acids Research, vol. 33, No. 17, pp. 1-9, (2005).
Marcel Margulies et al., "Genome sequencing in microfabricated high-density picolitre reactors," Nature, vol. 437, 51 pgs., Sep. 15, 2005.
Kristofer J. Thurecht et al., "Investigation of spontaneous microemulsion formation in supercritical carbon dioxide using high-pressure NMR," Journal of Supercritical Fluids, vol. 38, pp. 111-118, (2006).
Toshko Zhelev et al., "Heat Integration in Micro-Fluidic Devices," 16$^{th}$ European Symposium on Computer Aided Process Engineering and 9$^{th}$ International Symposium on Process Systems Engineering, pp. 1863-1868 published by Elsevier B.V. (2006).
Piotr Garstecki et al., "Formation of droplets and bubbles in a microfluidic T-junction—scaling and mechanism of break-up," Lab on a Chip, vol. 6, pp. 437-446, (2006).
Darren R. Link et al., "Electric Control of Droplets in Microfluidic Devices," Angewandte Chemie Int. Ed., vol. 45, pp. 2556-2560, (2006).
Peter Fielden et al., "Micro-Droplet Technology for High Throughout Systems and Methods," 1 pg., Mar. 8, 2006.
David Emerson et al., "Microfluidic Modelling Activities at C3M," Centre for Microfluidics & Microsystems Modelling, Daresbury Laboratory, pp. 1-26, May 15, 2006.
Richard Williams et al., "Amplification of complex gene libraries by emulsion PCR," Nature Methods, vol. 3, No. 7, pp. 545-550, Jul. 2006.
John H. Leamon et al., "Overview: methods and applications for droplet compartmentalization of biology," Nature Methods, vol. 3, No. 7, pp. 541-543, Jul. 2006.
Andrew D. Griffiths et al., "Miniaturising the laboratory in emulsion droplets," TRENDS in Biotechnology, vol. 24, No. 9, pp. 395-402, Jul. 14, 2006.
Jian-Bing Fan et al., "Highly parallel genomic assays," Nature Reviews/Genetics, vol. 7, pp. 632-644, Aug. 2006.
Jonas Jarvius et al., "Digital quantification using amplified single-molecule detection," Nature Methods, vol. 3, No. 9, pp. 15 pgs, Sep. 2006.
Kan Liu et al., "Droplet-based synthetic method using microflow focusing and droplet fusion," Microfluid Nanfluid, vol. 3, pp. 239-243, (2007), published online Sep. 22, 2006.
Dimitris Glotsos et al., "Robust Estimation of Bioaffinity Assay Fluorescence Signals," IEEE Transactions on Information Technology in Biomedicine, vol. 10, No. 4, pp. 733-739, Oct. 2006.
Kristofer J. Thurecht et al., "Kinetics of Enzymatic Ring-Opening Polymerization of □-Caprolactone in Supercritical Carbon Dioxide," Macromolecules, vol. 39, pp. 7967-7972, (2006).
Machiko Hori et al., "Uniform amplification of multiple DNAs by emulsion PCR," Biochemical and Biophysical Research Communications, vol. 352, pp. 323-328, (2007).
Frank Diehl et al., "Digital quantification of mutant DNA in cancer patients," Current Opinion in Oncology, vol. 19, pp. 36-42, (2007).
Delai L. Chen et al., "Using Three-Phase Flow of Immiscible Liquids to Prevent Coalescence of Droplets in Microfluidic Channels: Criteria to Identify the Third Liquid and Validation with Protein Crystallization," Langmuir, vol. 23, No. 4, pp. 2255-2260, (2007).
S. Mohr et al., "Numerical and experimental study of a droplet-based PCR chip," Microfluid Nanofluid, vol. 3, pp. 611-621, (2007).
Sigrun M. Gustafsdottir et al., "In vitro analysis of DNA-protein interactions by proximity ligation," PNAS, vol. 104, No. 9, pp. 3067-3072, Feb. 27, 2007.
Daniel J. Diekema et al., "Look before You Leap: Active Surveillance for Multidrug-Resistant Organisms," Healthcare Epidemiology • CID 2007:44, pp. 1101-1107 (Apr. 15), electronically published Mar. 2, 2007.
Charles N. Baroud et al., "Thermocapillary valve for droplet production and sorting," Physical Review E 75, 046302, pp. 046302-1-046302-5, Apr. 5, 2007.
Qinyu Ge et al., "Emulsion PCR-based method to detect Y chromosome microdeletions," Analytical Biochemistry, vol. 367, pp. 173-178, May 10, 2007.
Chunsun Zhang et al., "Miniaturized PCR chips for nucleic acid amplification and analysis: latest advances and future trends," Nucleic Acids Research, vol. 35, No. 13, pp. 4223-4237, Jun. 18, 2007.
Y. M. Dennis Lo et al., "Digital PCR for the molecular detection of fetal chromosomal aneuploidy," PNAS, vol. 104, No. 32, pp. 13116-13121, Aug. 7, 2007.
Helen R. Hobbs et al., "Homogeneous Biocatalysis in both Fluorous Biphasic and Supercritical Carbon Dioxide Systems," Angewandte Chemie, vol. 119, pp. 8006-8009, Sep. 6, 2007.
Nathan Blow, "PCR's next frontier," Nature Methods, vol. 4, No. 10, pp. 869-875, Oct. 2007.

(56) References Cited

OTHER PUBLICATIONS

Nicole Pamme, "continuous flow separations in microfluidic devices," Lab on a Chip, vol. 7, pp. 1644-1659, Nov. 2, 2007.
N. Reginald Beer et al., "On-Chip, Real-Time, Single-Coy Polymerase Chain Reaction in Picoliter Droplets," Analytical Chemistry, vol. 79, No. 22, pp. 8471-8475, Nov. 15, 2007.
Yuejun Zhao et al., "Microparticle Concentration and Separation by Traveling-Wave Dielectrophoresis (twDEP) for Digital Microfluidics," Journal of Microelectromechanical Systems, vol. 16, No. 6, pp. 1472-1481, Dec. 2007.
Sigma-Aldrich, "Synthesis of Mesoporous Materials," Material Matters, 3.1, 17, (2008).
Nick J. Carroll et al., "Droplet-Based Microfluidics for Emulsion and Solvent Evaporation Synthesis of Monodisperse Mesoporous Silica Microspheres," Langmuir, vol. 24, No. 3, pp. 658-661, Jan. 3, 2008.
Shia-Yen Teh et al., "Droplet microfluidics," Lab on a Chip, vol. 8, pp. 198-220, Jan. 11, 2008.
Chloroform (Phenomenex), Solvent Miscibility Table, Internet Archive WayBackMachine, 3 pgs., Feb. 1, 2008.
N. Reginald Beer et al., "On-Chip Single-Copy Real-Time Reverse-Transcription PCR in Isolated Picoliter Droplets," Analytical Chemistry, vol. 80, No. 6, pp. 1854-1858, Mar. 15, 2008.
Palani Kumaresan et al., "High-Throughput Single Copy DNA Amplification and Cell Analysis in Engineered Nanoliter Droplets," Analytical Chemistry, 17 pgs., Apr. 15, 2008.
Somil C. Mehta et a., "Mechanism of Stabilization of Silicone Oil—Water Emulsions Using Hybrid Siloxane Polymers," Langmuir, vol. 24, No. 9, pp. 4558-4563, Mar. 26, 2008.
Rhutesh K. Shah et al., "Polymers fit for function Making emulsions drop by drop," Materials Today, vol. 11, No. 4, pp. 18-27, Apr. 2008.
Mohamed Abdelgawad et al., "All-terrain droplet actuation," Lab on a Chip, vol. 8, pp. 672-677, Apr. 2, 2008.
Lung-Hsin Hung et al., "Rapid microfabrication of solvent-resistant biocompatible microfluidic devices," Lab on a Chip, vol. 8, pp. 983-987, Apr. 8, 2008.
Jenifer Clausell-Tormos et al., "Droplet-Based Microfluidic Platforms for the Encapsulation and Screening of Mammalian Cells and Multicellular Organisms," Chemistry & Biology, vol. 15, pp. 427-437, May 2008.
Vivienne N. Luk et al., "Pluronic Additives: A Solution to Sticky Problems in Digital Microfluidics," Langmuir, vol. 24, No. 12, pp. 6382-6289, May 16, 2008.
Yen-Heng Lin et al., "Droplet Formation Utilizing Controllable Moving-Wall Structures for Double-Emulsion Applications," Journal of Microelectromechanical Systems, vol. 17, No. 3, pp. 573-581, Jun. 2008.
Simant Dube et al., "Mathematical Analysis of Copy Number Variation in a DNA Sample Using Digital PCR on a Nanofluidic Device," PLoS One, vol. 3, Issue 8, pp. 1-9, Aug. 6, 2008.
Jian Qin et al., "Studying Copy Number variations using a nanofluidic platform," Nucleic Acids Research, vol. 36, No. 18, pp. 1-8, Aug. 18, 2008.
C. Holtze et al., "Biocompatible surfactants for water-in-fluorocarbon emulsions," Lab on a Chip, vol. 8, pp. 1632-1639, Sep. 2, 2008.
Margaret Macris Kiss et al., "High-Throughput Quantitative Polymerase Chain Reaction in Picoliter Droplets," Analytical Chemistry, 8 pgs., downloaded Nov. 17, 2008.
Jay Shendure et al., "Next-generation DNA sequencing," Nature Biotechnology, vol. 26, No. 10, pp. 1135-1145, Oct. 2008.
Bernhard G. Zimmermann et al., "Digital PCR: a powerful new tool for noninvasive prenatal diagnosis?," Prenatal Diagnosis, vol. 28 pp. 1087-1093, Nov. 10, 2008.
Avishay Bransky et al., "A microfluidic droplet generator based on a piezoelectric actuator," Lab on a Chip, vol. 9, pp. 516-520, Nov. 20, 2008.
David A. Weitz, "Novel Surfactants for Stabilizing Emulsions of Water or Hydrocarbon Oil-Based Droplets in a Fluorocarbon Oil Continuous Phase," Harvard Office of Technology Development: Available Technologies, pp. 1-3, downloaded Nov. 28, 2008.
Neil Reginald Beer et al., "Monodisperse droplet generation and rapid trapping for single molecule detection and reaction kinetics measurement," Lab on a Chip, vol. 9, pp. 841-844, Dec. 5, 2008.
Richard M. Cawthon, "Telomere length measurement by a novel monochrome multiplex quantitative PCR method," Nucleic Acids Research, vol. 37, No. 3, pp. 1-7, (2009).
Anthony J. O'Lenick, Jr., "Silicone Emulsions and Surfactants—A Review," Silicone Spectator, Silitech LLC, May, 2009 (original published May 2000).
Adam R. Abate et al., "Functionalized glass coating for PDMS microfluidic devices," Lab on a Chip Technology: Fabrication and Microfluidics, 11 pgs., (2009).
Chia-Hung Chen et al., "Janus Particles Templated from Double Emulsion Droplets Generated Using Microfluidics," Langmuir, vol. 29, No. 8, pp. 4320-4323, Mar. 18, 2009.
Luis M. Fidalgo et al., "Coupling Microdroplet Microreactors with Mass Spectrometry: Reading the Contents of Single Droplets Online," Angewandte Chemie, vol. 48, pp. 3665-3668, Apr. 7, 2009.
Linas Mazutis et al., "A fast and efficient microfluidic system for highly selective one-to-one droplet fusion," Lab on a Chip, vol. 9, pp. 2665-2672, Jun. 12, 2009.
Linas Mazutis et al., "Droplet-Based Microfluidic Systems for High-Throughput Single DNA Molecule Isothermal Amplification and Analysis," Analytical Chemistry, vol. 81, No. 12, pp. 4813-4821, Jun. 15, 2009.
Frank McCaughan et al., "Single-molecule genomics," Journal of Pathology, vol. 220, pp. 297-306, Nov. 19, 2009.
Suzanne Weaver et al., "Taking qPCR to a higher level: Analysis of CNV reveals the power of high throughput qPCR to enhance quantitative resolution," Methods, vol. 50, pp. 271-276, Jan. 15, 2010.
Amelia L. Markey et al., "High-throughput droplet PCR," Methods, vol. 50, pp. 277-281, Feb. 2, 2010.
Yoon Sung Nam et al., "Nanosized Emulsions Stabilized by Semi-solid Polymer Interphase," Langmuir, ACS Publications, Jul. 23, 2010.
Tatjana Schütze et al., "A streamlined protocol for emulsion polymerase chain reaction and subsequent purification," Analytical Biochemistry, vol. 410, pp. 155-157, Nov. 25, 2010.
Somanath Bhat et al., "Effect of sustained elevated temperature prior to amplification on template copy number estimation using digital polymerase chain reaction," Analyst, vol. 136, pp. 724-732, (2011).
James G. Wetmur, et al., "Linking Emulsion PCR Haplotype Analysis," PCR Protocols, Methods in Molecular Biology, vol. 687, pp. 165-175, (2011).
Paul Vulto et al., "Phaseguides: a paradigm shift in microfluidic priming and emptying," Lab on a Chip, vol. 11, No. 9, pp. 1561-1700, May 7, 2011.
Thinxxs Microtechnology AG, "Emerald Biosystems: Protein Crystallization," 1 pg., downloaded Mar. 8, 2011.
Qun Zhong et al., "Multiplex digital PCR: breaking the one target per color barrier of quantitative PCR," Lab on a Chip, vol. 11, pp. 2167-2174, (2011).
Jiaqi Huang et al., "Rapid Screening of Complex DNA Samples by Single-Molecule Amplification and Sequencing," PLoS One, vol. 6, Issue 5, pp. 1-4, May 2011.
Burcu Kekevi et al., Synthesis and Characterization of Silicone-Based Surfactants as Anti-Foaming Agents, J. Surfact Deterg (2012), vol. 15, pp. 73-81, published online Jul. 7, 2011.
Leonardo B. Pinheiro et al., "Evaluation of a Droplet Digital Polymerase Chain Reaction Format for DNA Copy Number Quantification," Analytical Chemistry, vol. 84, pp. 1003-1011, Nov. 28, 2011.
Nicole L. Solimini et al., "Recurrent Hemizygous Deletions in Cancers May Optimize Proliferative Potential," Science, vol. 337, pp. 104-109, Jul. 6, 2012.
Labsmith, "Microfluid Components" webpage, downloaded Jul. 11, 2012.
Labsmith, "CapTite™ Microfluidic Interconnects" webpage, downloaded Jul. 11, 2012.
Nathan A. Tanner et al., "Simultaneous multiple target detection in real-time loop-mediated isothermal amplification," BioTechniques, vol. 53, pp. 819, Aug. 2012.
Nora Lindner, Authorized Officer, The International Bureau of WIPO, "International Preliminary Report on Patentability," in connection with related PCT Patent App. No. PCT/US2011/030077, 9 pgs., Sep. 25, 2012.

\* cited by examiner

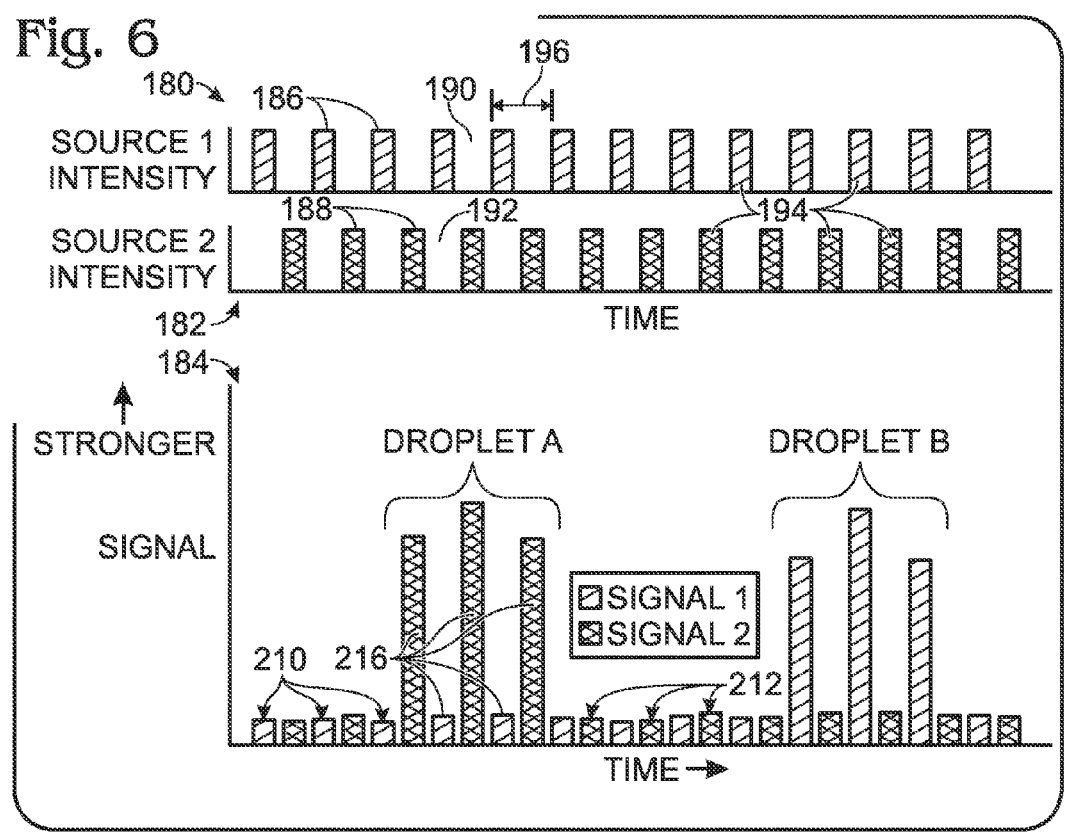

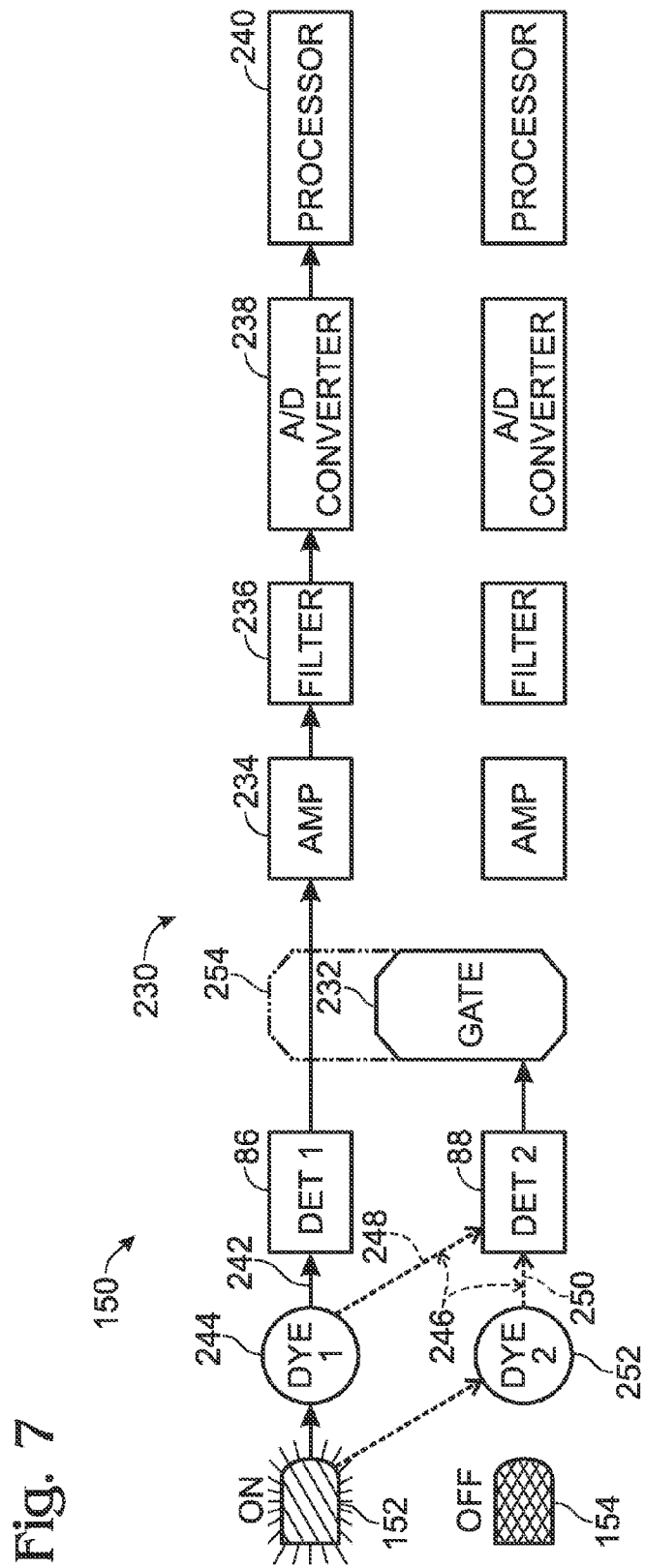

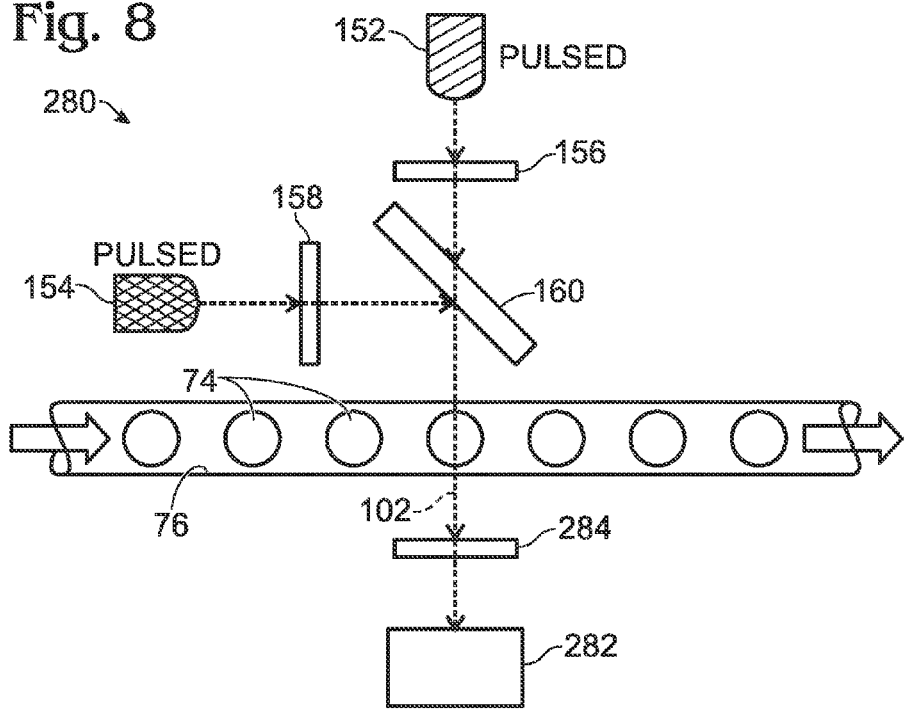
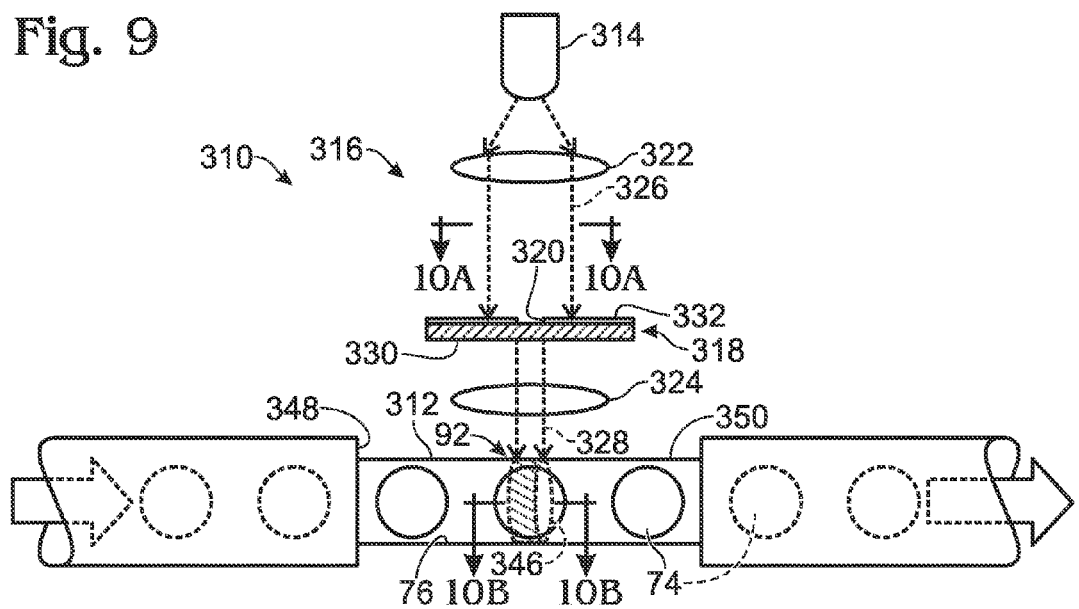

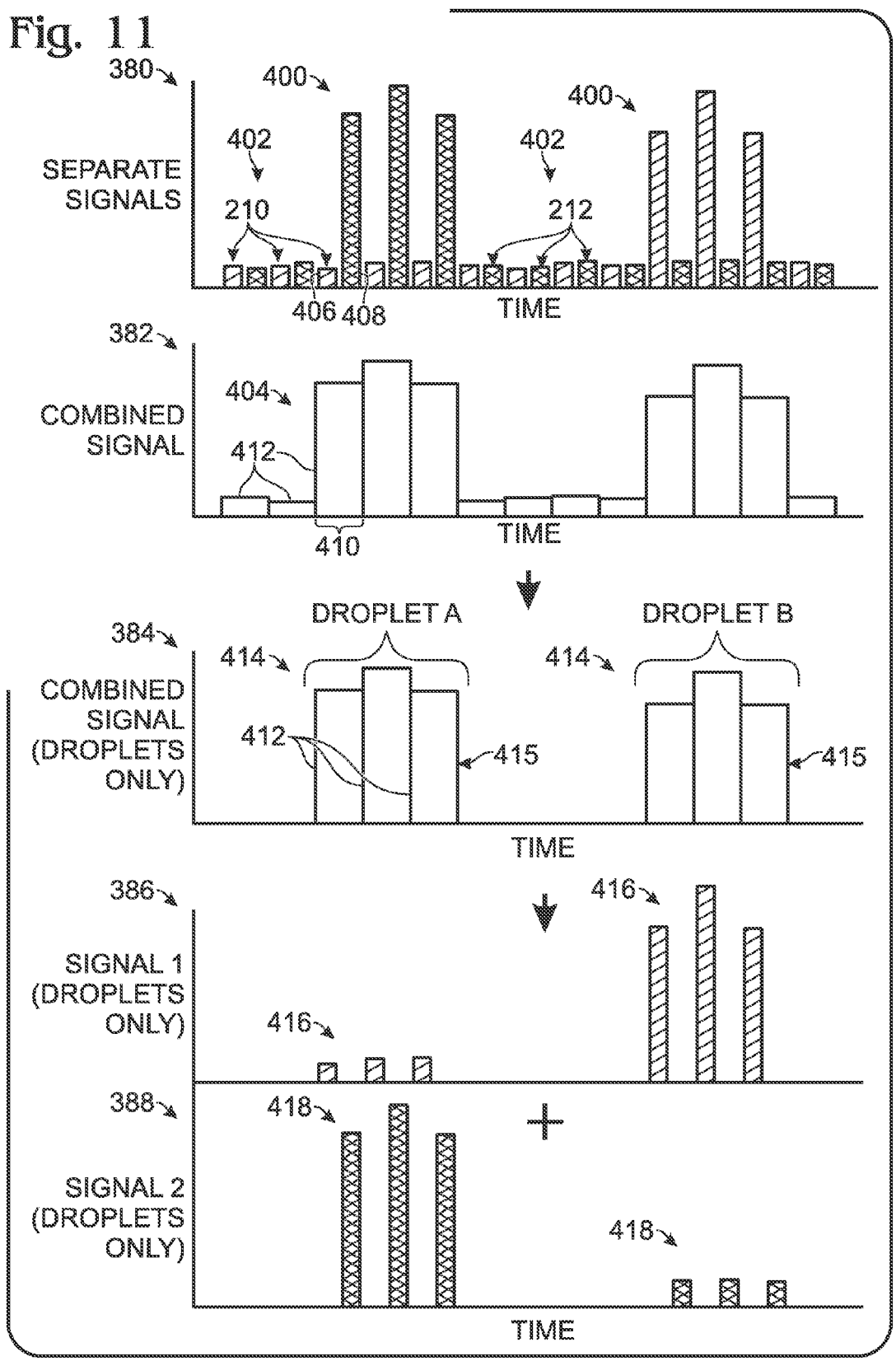

DETECTION SYSTEM FOR DROPLET-BASED ASSAYS

CROSS-REFERENCE TO PRIORITY APPLICATION

This application is a continuation of PCT Patent Application Serial No. PCT/US2011/030077, filed Mar. 25, 2011, which, in turn, claims the benefit under 35 U.S.C. §119(e) of U.S. Provisional Patent Application Ser. No. 61/317,684, filed Mar. 25, 2010. Each of these priority applications is incorporated herein by reference in its entirety for all purposes.

CROSS-REFERENCES TO OTHER MATERIALS

This application incorporates by reference in their entireties for all purposes the following materials: U.S. Pat. No. 7,041,481, issued May 9, 2006; U.S. Patent Application Publication No. 2010/0173394 A1, published Jul. 8, 2010; and Joseph R. Lakowicz, PRINCIPLES OF FLUORESCENCE SPECTROSCOPY ($2^{nd}$ Ed. 1999).

INTRODUCTION

Many biomedical applications rely on high-throughput assays of samples. For example, in research and clinical applications, high-throughput genetic tests using target-specific reagents can provide high-quality information about samples for drug discovery, biomarker discovery, and clinical diagnostics, among others. As another example, infectious disease detection often requires screening a sample for multiple genetic targets to generate high-confidence results.

Emulsions hold substantial promise for revolutionizing high-throughput assays. Emulsification techniques can create billions of aqueous droplets that function as independent reaction chambers for biochemical reactions. For example, an aqueous sample (e.g., 200 microliters) can be partitioned into droplets (e.g., four million droplets of 50 picoliters each) to allow individual sub-components (e.g., cells, nucleic acids, proteins) to be manipulated, processed, and studied discretely in a massively high-throughput manner.

Aqueous droplets can be suspended in oil to create a water-in-oil emulsion (W/O). The emulsion can be stabilized with a surfactant to reduce or prevent coalescence of droplets during heating, cooling, and transport, thereby enabling thermal cycling to be performed. Accordingly, emulsions have been used to perform single-copy amplification of nuclei acid target molecules in droplets using the polymerase chain reaction (PCR). The fraction of the droplets that are positive for a target can be analyzed with Poisson statistics to estimate the concentration of the target in a sample.

Droplet-based assays often use one or more fluorophores as labels in droplets to report the occurrence of a reaction, such as amplification, and thus the presence or absence of at least one copy of a target in individual droplets. The droplets may be generated and reacted (e.g., thermally cycled), and then light emission is measured from each droplet to determine whether or not a target is present in the droplet. The presence or absence of multiple different targets can be measured in each droplet if a different, distinguishable fluorophore serves as a reporter for each different target. However, there are many technical hurdles to producing a light detection system for droplets that is relatively low cost, capable of distinguishably detecting two or more colors (fluorescence from two or more distinct fluorophores) at a single point, collects droplet data of high resolution, works with popular dyes (such as FAM and VIC dyes), and/or efficiently identifies droplets within a signal.

Improved light detection systems for droplets are needed.

SUMMARY

The present disclosure provides a system, including methods and apparatus, for light detection and signal processing for droplet-based assays.

BRIEF DESCRIPTION OF THE DRAWINGS

FIG. 6 is a series of graphs illustrating how exemplary data collected with the detection system of FIG. 5 correspond with pulses of illumination generated by an illumination assembly of the system, in accordance with aspects of present disclosure.

FIG. 7 is a schematic view of selected aspects of an exemplary controller for the system of FIG. 5, with the controller collecting data from only one of the corresponding pairs of light source and detector based on which light source is providing illumination of the examination region, in accordance with aspects of the present disclosure.

FIG. 8 is a schematic view of selected aspects of yet another exemplary detection system for droplet-based assays, in accordance with aspects of the present disclosure.

FIG. 9 is a schematic view of selected aspects of an exemplary illumination assembly and capillary that may be included in the signal detection systems disclosed herein.

FIG. 11 is a series of graphs illustrating an exemplary approach to processing data collected with the detection systems disclosed herein, in accordance with aspects of the present disclosure.

DETAILED DESCRIPTION

Figure 1:
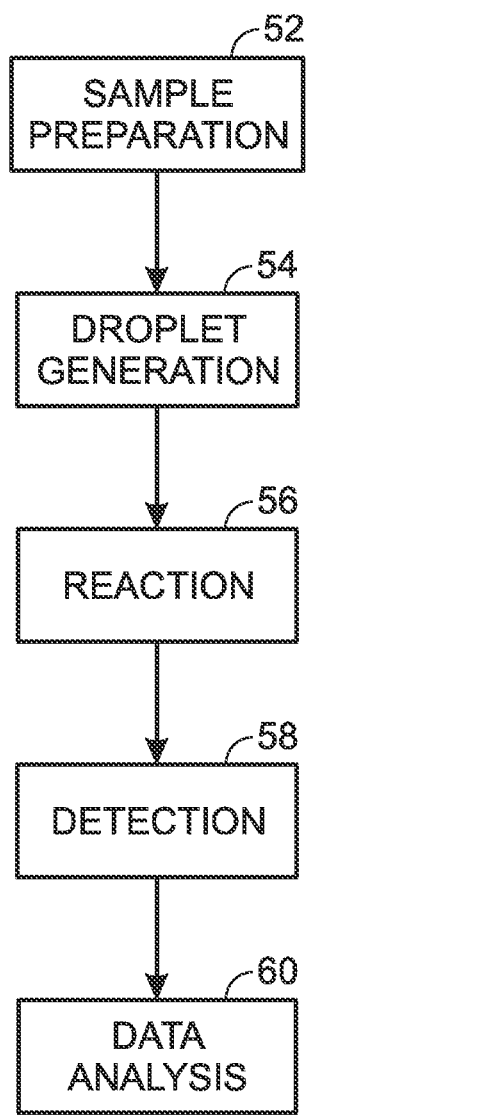
FIG. 1 is a flowchart listing exemplary steps that may be performed in a droplet-based assay, in accordance with aspects of the present disclosure.

The present disclosure provides a system, including methods and apparatus, for light detection and signal processing for droplet-based assays.

A method of detection for droplets in provided. In the method, an examination region of a channel may be illuminated with first pulses of light interleaved with second pulses of light as droplets pass through the examination region. The first pulses may be spectrally distinct from the second pulses. Data representing light detected during illumination of the examination region with the first pulses and the second pulses may be collected.

Another method of detection for droplets is provided. In the method, an examination region of a channel may be illuminated alternately with pulses of light emitted by a first light source and a second light source as droplets pass through the examination region. Light may be detected from the examination region illuminated by the pulses of light. A first signal and a second signal may be generated. The first signal may represent light detected at least predominantly when the first region is illuminated with pulses of light from the first light source, and the second signal may represent light detected at least predominantly when the second region is illuminated with pulses of light from the second light source.

A system for detection for droplet-based assays is provided. The system may comprise a channel and an illumination assembly. The illumination assembly may be configured to illuminate an examination region of the channel with first pulses of light interleaved with second pulses of light as droplets pass through the examination region. The first pulses may be spectrally distinct from the second pulses. The system also may comprise one or more detectors configured to detect light from the examination region and may further comprise a controller that collects data representing light detected during illumination of the examination region with the first pulses and the second pulses.

Another system for detection for droplet-based assays is provided. The system may comprise a channel and an illumination assembly configured to produce a beam of light that illuminates an examination region of the channel as droplets pass through such region. The system also may comprise a detector configured to detect light received from the examination region and a controller that collects data representing light detected by the detector. The beam of light may be elongated in cross section where the beam intersects the channel.

Yet another system for detection for droplet-based assays is provided. The system may comprise a channel and a light source that illuminates an examination region of the channel as droplets pass through such region. The system also may comprise a detector configured to detect light received from the examination region and a controller that collects data representing light detected by the detector. Light emitted by the light source may travel through at least one slit between the light source and the detector.

Still another method of detection for droplets is provided. In the method, an examination region of a channel may be illuminated with a beam of light that is elongated in cross section. Data representing light detected over time from the region may be collected as a plurality of droplets pass through the examination region.

Another method of detection for droplet-based assays is provided. In the method, at least two separate signals may be generated, with each separate signal representing light detected with a different detection configuration during a series of time intervals from a stream of fluid carrying droplets. The at least two separate signals may be combined to form a combined signal. The combined signal may be processed to identify time intervals that correspond to droplets.

Yet another method of detection for droplet-based assays is provided. In the method, at least two separate signals may be generated, with each separate signal representing a respective different wavelength or waveband of light detected during a series of time intervals from a stream of fluid carrying droplets. Light detected from each wavelength or waveband may report the presence or absence of a different target in individual droplets. The at least two separate signals may be combined to form a combined signal. The combined signal may be processed to identify time intervals that correspond to droplets. Droplets containing each different target may be determined based on values of each separate signal detected during the identified time intervals.

Still another method of detection for droplet-based assays is provided. In the method, at least two signals may be generated, with each signal representing a respective different waveband of light detected during a series of time intervals from a stream of fluid with droplets. Values of the at least two signals may be combined to form a combined signal. Portions of the combined signal that correspond to droplets may be identified. Values of each of the at least two signals may be processed, with the values corresponding to the portions identified, to determine which droplets contain each target.

Another system for detection for droplet-based assays is provided. The system may comprise one or more detectors configured to detect light from a stream of fluid carrying droplets containing at least two different dyes. The system also may comprise a controller configured to generate separate signals each representing light detected with a different detection configuration during a series of time intervals from a stream of fluid carrying droplets, to combine the at least two separate signals to form a combined signal, and to process the combined signal to identify time intervals that correspond to droplets.

Still yet another method of detection for droplets is provided. In the method, droplets may be obtained, with the droplets including a first dye and a second dye. An emission spectrum of the first dye and an absorption spectrum of the second dye may define a waveband of overlap and overlap sufficiently to produce at least half-maximal emission from the first dye if the first dye is excited at a maximal absorption wavelength of the second dye. The droplets may be illuminated with excitation light capable of exciting the first dye and the second dye, with the excitation light being emitted by one or more LEDs and including only a shorter-wavelength segment of the waveband of overlap. Light emitted by the first dye and the second dye may be detected. Light emitted from the second dye may be detected in a wavelength range including only a longer-wavelength segment of the waveband of overlap that is spaced from the shorter-wavelength segment.

Another method of detection for droplets is provided. In the method, a beam of light may be generated. The beam of light may be split into a main beam and at least one sampling beam. An intensity of the sampling beam may be monitored. An intensity of the beam of light may be adjusted based on one or more measurements from the step of monitoring. An examination region of a channel may be illuminated with light from the main beam as droplets pass through the examination region. Data representing light detected from the examination region may be collected.

Further aspects of the present disclosure are described in the following sections: (I) overview of detection systems for droplet-based assays, (II) detection system with pulsed illumination, (III) detection unit with a slit, (IV) droplet identification with combined signals, (V) optical layout for a detection unit, (VI) detection system with spaced examination sites, and (VII) selected embodiments.

I. Overview of Detection Systems for Droplet-Based Assays

FIG. 1 shows an exemplary system 50 for performing a droplet-, or partition-, based assay. In brief, the system may include sample preparation 52, droplet generation 54, reaction (e.g., amplification) 56, detection 58, and data analysis 60. The system may be utilized to perform a digital PCR (polymerase chain reaction) analysis. More specifically, sample preparation 52 may involve collecting a sample, such as a clinical or environmental sample, treating the sample to release associated nucleic acids, and forming a reaction mixture involving the nucleic acids (e.g., for amplification of a target nucleic acid). Droplet generation 54 may involve encapsulating the nucleic acids in droplets, for example, with about one copy of each target nucleic acid per droplet, where the droplets are suspended in an immiscible carrier fluid, such as oil, to form an emulsion. Reaction 56 may involve subjecting the droplets to a suitable reaction, such as thermal cycling to induce PCR amplification, so that target nucleic acids, if any, within the droplets are amplified to form additional copies. Detection 58 may involve detecting some signal(s), such as radiation, from the droplets indicative of whether or not there was amplification. Finally, data analysis 60 may involve estimating a concentration of the target nucleic acid in the sample based on the percentage (e.g., the fraction) of droplets in which amplification occurred. The detection systems disclosed herein may perform any suitable combination of the steps of FIG. 1, in any suitable order, but particularly may perform detection 58 and/or data analysis 60. Further aspects of droplet-based assay systems that may be suitable for the detection systems of the present disclosure are described in the Cross-References listed above, which are incorporated herein by reference, particularly U.S. Provisional Patent Application Ser. No. 61/317,684, filed Mar. 25, 2010; U.S. Pat. No. 7,041,481, issued May 9, 2006; and U.S. Patent Application Publication No. 2010/0173394 A1, published Jul. 8, 2010.

Droplet-based assay systems, and detection step 58 in particular, generally may involve sensing or detecting droplets themselves and/or contents of the droplets. The detection of droplets themselves may include determining the presence or absence of a droplet (or a plurality of droplets) and/or a characteristic(s) of the droplet, such as its size (e.g., radius or volume), shape, type, and/or aggregation state, among others. The detection of the contents of droplets may include determining the nature of the contents (e.g., whether or not the droplet contains a target(s)) and/or a characteristic of the contents (e.g., whether or not the contents have undergone a reaction, such as PCR, the extent of any such reaction, etc.). The detection of droplets and their contents, if both are detected, may be performed independently or coordinately, in any suitable order. For example, the detection may be performed serially (one droplet at a time), in parallel, in batch, and so forth.

Detection generally may be performed using any technique(s) or mechanism(s) capable of yielding, or being processed to yield, the desired information. These mechanisms may include optical techniques (e.g., measuring absorbance, transmission, reflection, scattering, birefringence, dichroism, fluorescence, phosphorescence, etc.), electrical techniques (e.g., measuring bulk resistance, conductance, capacitance, etc.), and/or acoustic techniques (e.g., ultrasound), among others. The fluorescence techniques, in turn, may include fluorescence intensity, fluorescence polarization (or fluorescence anisotropy) (FP), fluorescence correlation spectroscopy (FCS), fluorescence recovery after photobleaching (FRAP), total internal reflection fluorescence (TIRF), fluorescence resonance energy transfer (FRET), fluorescence lifetime, and/or fluorescence imaging, among others.

Figure 2:
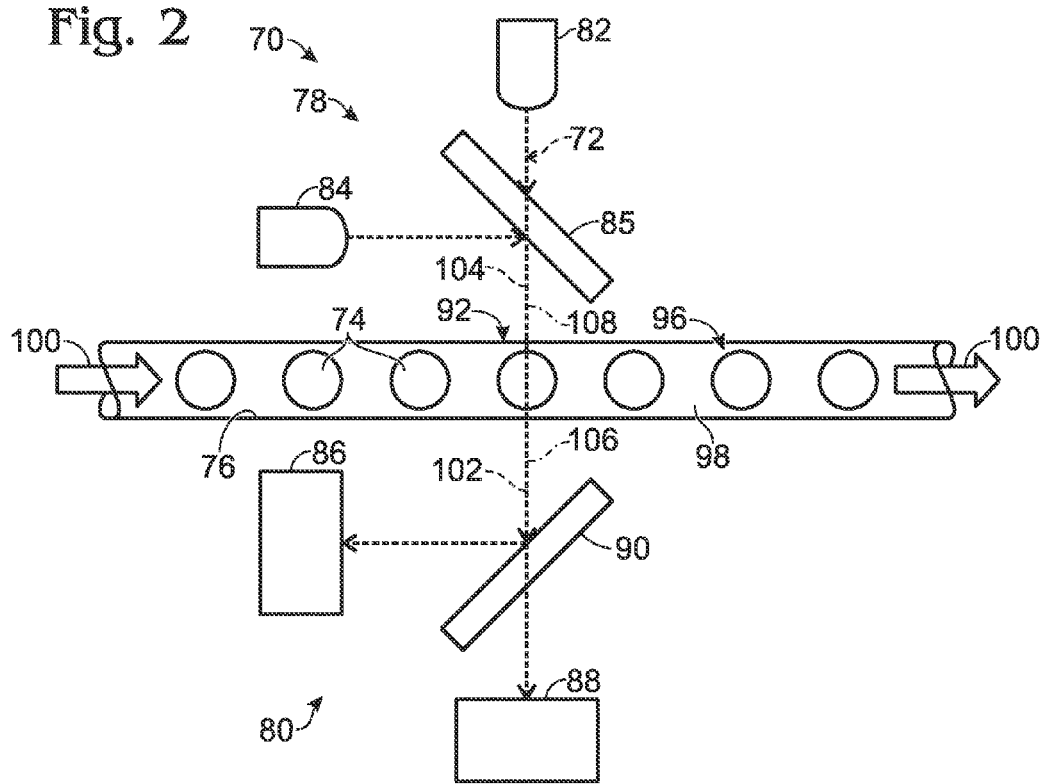
FIG. 2 is a schematic view of selected aspects of an exemplary detection unit including an illumination assembly to irradiate droplets with light and a collection assembly to gather and detect light from the droplets, in accordance with aspects of the present disclosure.

FIG. 2 shows an exemplary detection unit 70 for detecting light 72 from droplets 74 disposed in a channel 76. The detection unit may include at least one illumination assembly 78 and at least one collection assembly 80. Light may include ultraviolet radiation, visible light, infrared radiation, or any combination thereof.

The droplets may have any suitable diameter relative to the channel. For example, the droplets may have about the same diameter as the channel (e.g., slightly larger or smaller than the channel). With this relative size arrangement, each droplet may be substantially centered in the channel, thereby avoiding variability in measurements that may be produced by off-center droplets. Alternatively, the diameter of the channel may be substantially greater than the diameter of the droplets, such as at least about 50% greater. In this case, some of the droplets may be off-center when they are detected, which may change the signal intensity.

Illumination assembly 78 illuminates channel 76 with at least one beam of light (also termed radiation) produced by at least one light source, such as light sources 82, 84. Illumination also or alternatively may be described as irradiation, and a light source as a radiation source. Exemplary light sources include light-emitting diodes (LEDs), lasers, and so on. Each light source may be an excitation source configured to emit radiation at a particular wavelength or range of wavelengths. Each source in a multiple source excitation system may (or may not) be configured to emit radiation having a different spectral signature, to react with fluorophores that are responsive to those various signatures. For example, the excitation sources may be LEDs configured to emit radiation with peak amplitudes at different frequencies, i.e., radiation of different colors. Light from each light source may be transmitted to channel 76 via illumination optics 85. The illumination optics may modify the spectral signature of light emitted by each light source, such as by limiting the range of wavelengths used for illumination.

Collection assembly 80 gathers and detects light from channel 76, such as light produced in response to illumination of the channel by illumination assembly 78. Collection assembly 80 may include at least one detector, such as detectors 86, 88, and collection optics 90 that transmit light from the channel to the detector(s). Exemplary detectors include photomultiplier tubes (PMTs), photodiodes, avalanche photodiodes, charge-coupled devices (CCDs), CMOS devices, or the like. Accordingly, each detector may be a point detector or an imaging detector. At least one of the detectors may be a scatter detector configured to detect scattered light, such as light that is forward-scattered. A scatter detector can provide information about droplet sizes (e.g., volume and/or diameter), in some cases with the assumption that droplets are traveling at a constant velocity. Further aspects of scatter detectors and detection of light scattered from droplets are described in U.S. Patent Application Publication No. 2010/0173394 A1, published Jul. 8, 2010, which is incorporated herein by reference.

Illuminations optics 85 and collection optics 90 each may include one or more optical elements that transmit light from each light source to channel 76 (for optics 85) or from the channel to each detector (for optics 90). Accordingly, the illumination optics may define an optical path traveled by light from each light source to the channel, and the collection optics may define an optical path traveled by light from the channel to each detector. Each optical path may be branched or unbranched. If two or more light sources are used in the detection unit, illumination optics 85 may combine beams from the light sources, such that radiation incident on the channel is a combined beam from multiple light sources. In a combined beam, individual beams from the light sources overlap one another. If two or more detectors are used in the detection unit, collection optics 90 may split collected light (e.g., emission light) received from the channel, to send a portion of the collected light to each detector. In some cases, within a single detection unit, the illumination optics may combine beams from multiple light sources, and the collection optics may distribute collected light between or among multiple detectors. Alternatively, in some embodiments, the illumination optics may combine beams, or the collection optics may split a collected beam, but not both.

An optical element can be any structure or device that collects, directs, and/or focuses light and/or selectively blocks undesired light, among others. An optical element may function by any suitable mechanism, such as light refraction, reflection, diffraction, blocking, and/or filtering, among others. Exemplary optical elements include lenses, mirrors, gratings, prisms, filters, beam splitters, transmissive fibers (fiber optics), apertures, diffusers, or the like. The walls of the channel 76 also may act as an optical element. For example, the channel may be defined by a tube forming a cylindrical lens that helps to focus light for illumination for collection.

In some cases, illumination optics and/or collection optics are not used in the detection unit. For example, a light beam from a light source may travel directly to the channel without being transmitted by any interposed optical element(s). Alternatively, or in addition, light from the channel may travel directly to a detector (e.g., a detector close to the channel) without being transmitted by any interposed optical element(s).

The illumination assembly and collection assembly collectively define an examination region 92 of the channel. The examination region includes any portion or portions of the channel illuminated by the illumination assembly (or assemblies), from which light is detected by the collection assembly (or assemblies). Accordingly, an examination region may be continuous or may be discontinuous, with two or more spaced examination sites forming the examination region. In some cases, at least two light sources (and/or pulses of light that are spectrally distinct from each other) may illuminate overlapping portions or volumes of an examination region and/or at least two detectors may detect light from overlapping portions or volumes of the examination region. The overlapping portions can be considered the same portion if there is more than 50% overlap.

Droplets 74 may be a dispersed phase of an emulsion 96 including a continuous phase 98. The emulsion, and the droplets and continuous phase thereof, may be driven, indicated by motion arrows at 100, along the channel through examination region 92. Accordingly, light may be detected from a stream of fluid carrying droplets, with droplets passing, such as serially as shown here, through the examination region. The droplets may travel through the examination region in single file and spaced from each other, to permit detection of light from individual droplets as each passes through the examination region. The droplets may be separated from one another by travel through at least one spacer (also termed a singulator) disposed upstream of the examination region. The spacer, which may be a flow-focusing region, may place droplets in single file. The spacer also or alternatively may dilute the emulsion in which the droplets are disposed, by adding a carrier fluid (e.g., additional continuous phase) to the emulsion. Exemplary structures for the spacer are shaped as a cross and a T, among others. The examination region may be relatively close to the spacer, such as less than about 100, 50, 25, or 10 droplet or channel diameters from a separation region or confluence region of the spacer.

Collected light 102 (e.g., emitted light) from the droplets (and/or emulsion) may be generated in response to incident light 104 (e.g., excitation light) from the illumination assembly. The respective optical paths 106, 108 of collected light 102 from the channel and incident light 104 to the channel may have any suitable directional relationship. Here, to simplify the presentation, the optical paths of incidence (106) and collection (108) are shown as being in a trans configuration, with illumination and collection performed on opposing sides of the channel. In other exemplary configurations, collection may be performed transversely (e.g., orthogonally) to illumination or in an epi configuration, where the directions of illumination and collection are anti-parallel to each another.

Detection unit 70 may include any suitable combination of one or more light sources and one or more detectors. For example, a single light source may be used with a single detector, a single light source may be used with multiple detectors, two or more light sources may be used with a single detector, or two or more light sources may be used with two or more detectors.

In some embodiments, detection unit 70 may include only one light source 82 configured to emit radiation at a particular wavelength or range of wavelengths, and at least two detectors 86, 88. Collection optics 90 may split radiation collected from examination region 92, to provide a suitable portion of the radiation for each detector. The radiation emitted by an illuminated droplet may be split by a beam-splitter and/or filtered by one or more filters, so that only radiation within a particular wavelength regime will arrive at a particular detector. This allows detection of multiple dyes with potentially overlapping emission spectra. If one or more targets are present in an illuminated droplet, reporters for those targets will be excited by incident radiation from the single light source and will fluoresce at a particular wavelength or range of wavelengths. The signature (i.e., color) of the resulting fluorescence will depend upon which target or combination of targets was present in the droplet.

The one or more detection units of a detection system may illuminate the examination region with any suitable wavelengths of light. The light may be ultraviolet radiation, visible light, infrared radiation, or any combination thereof, in overlapping or separate illumination volumes. Also, the detection units may detect light of any suitable wavelength, such as ultraviolet radiation, visible light, and/or infrared radiation, from overlapping or separate detection volumes. For example, in some embodiments, the droplets may include an absorbing or fluorescent dye that absorbs and/or emits in the infrared range (e.g., near infrared or shortwave infrared, among others) upon excitation or illumination with ultraviolet radiation, visible light, or infrared radiation. The infrared dye may be a droplet marker used to identify droplet regions (and thus droplets) in a signal representative of detected infrared radiation and/or may serve an internal reference for instrument calibration (e.g., adjusting the detector gain). Alternatively, the infrared dye may a reporter (e.g., a probe) for a target in the droplets. The use of an infrared dye expands the range of wavelengths available for detection and thus may enable a higher level of multiplexing, more accurate droplet identification, or a combination thereof, among others.

One or more detection units may provide multiple detection configurations that are different from each other. A detection configuration generally includes an operative combination of a light source, illumination optics (if used), collection optics (if used), and a detector. Accordingly, different detection configurations may be created by changing the light source used for illumination, the wavelength filter(s) (if any) used to filter illumination light from the light source, the wavelength filter(s) (if any) used to filter light collected from the examination site, the detector, or any combination thereof, among others. In some cases, separate signals may be generated from respective different detection configurations and/or multiple signals may be generated from a corresponding number of different detection configurations. With two or more detection configurations, each detection configuration may have different sensitivities to dyes present in droplets. For example, in an assay with two dyes, two separate signals generated from two different detection configurations may be deconvolved to infer dye-specific signals.

Figure 3:
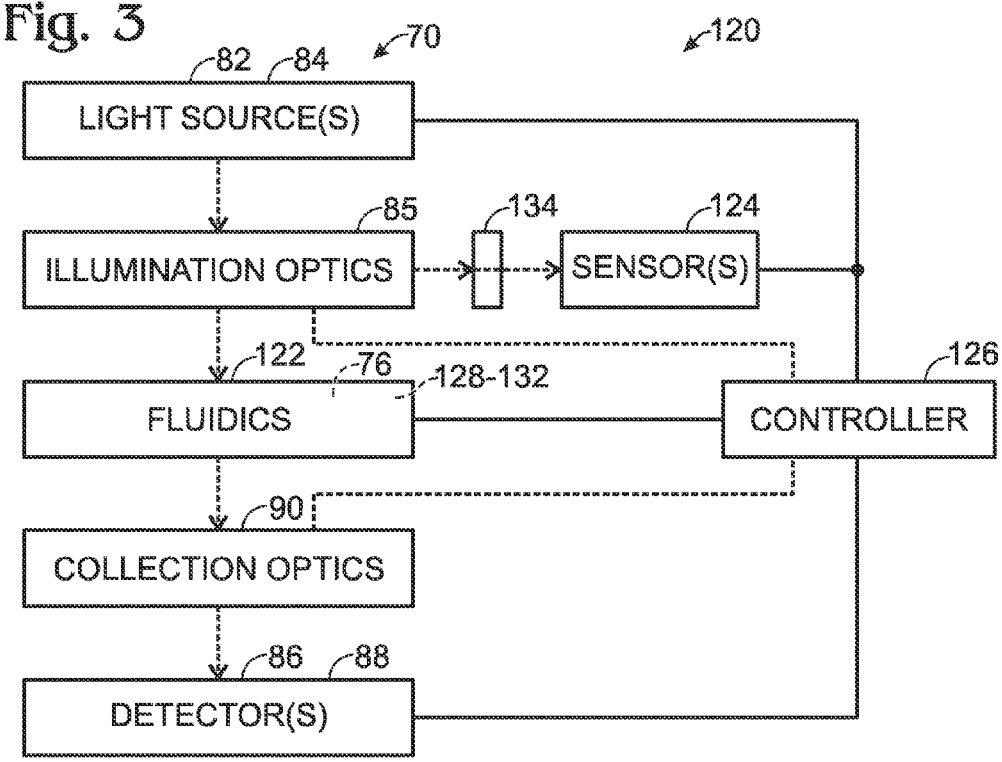
FIG. 3 is a schematic view of an exemplary detection system including the detection unit of FIG. 2, in accordance with aspects of present disclosure.

FIG. 3 shows an exemplary detection system 120 including detection unit 70 of FIG. 2. The detection system also may include fluidics 122, one or more feedback sensors 124 (also termed monitoring sensors) for the illumination assembly, and at least one controller 126.

Fluidics 122 may include any suitable combination of fluidic elements in addition to channel 76. These fluidic elements may include least one pump 128 to drive flow of fluid through the channel, one or more valves 130 to regulate or direct flow into, through, and/or out of the channel, other channels that communicate with channel 76, or the like. The other channels may include one or more dilution channels that add a dilution fluid, to separate droplets from each other at one or more droplet spacers (e.g., a T-shaped or cross-shaped spacer/singulator 132), disposed upstream of the examination region.

A feedback sensor 124 may detect the intensity of a sample of light from each light source. In some cases, the illumination optics may split the beam from the light source(s) into an illumination beam and a sampling beam. The sampling beam may be directed to feedbacks sensor 124, instead of channel 76, via sampling optics 134. The sensor monitors the intensity of the sampling beam, which may be proportional to the intensity of the illumination beam. The sampling beam may be split from a main beam of light from a light source at any position along the optical path of the illumination optics, such as before or after a waveband for illumination has been defined by one or more filters. Intensity information from sensor 124 may be communicated to controller 126, which may adjust the voltage or power supplied to the light source, to maintain a more constant intensity of the light source over time, such as within an assay or between assays. In other words, the light source, feedback sensor, and controller may form a feedback loop to maintain a more constant intensity of illumination with changes in temperature, light source age, etc. Positioning the feedback sensor after the illumination waveband has been defined may be particularly advantageous, because some light sources (such as LEDs) may exhibit a wavelength shift in their emission maximum with changes in temperature or age, among others. By detecting sampled light after waveband definition, the feedback loop can maintain a more uniform intensity of illumination, because any effect of spectral change on illumination intensity is measured by the sensor. Exemplary feedback sensors include any of the detectors disclosed herein, such as a photodiode, among others. Further aspects of monitoring light source intensities are described below in Section V.

Controller 126 may control operation of, receive inputs from, and/or otherwise communicate with any other components of the system, such as the light sources, illumination optics, fluidics, collection optics, detectors, feedback sensors, or any combination thereof. For example, the controller may control when and how much power is supplied to each light source (e.g., to control when each light source is turned on and off), the sensitivity of each detector (e.g., by adjusting the gain), creation of signals from detected light, a shuttering function of the optics, and/or any combination thereof. Alternatively, or in addition, the controller may control generation of detector-specific and/or periodic signals, may process signals for droplet identification, may determine whether each identified droplet should be excluded from an analysis and/or contains one or more targets, may estimate one or more target concentrations, or any combination thereof, among others. The controller may include one or more processors (e.g., digital processors, also termed central/computer processing units (CPUs)) for data processing and also may include additional electronic components to support and/or supplement the processors, such as amplifiers, frequency filters, analog to digital converters, busses, one or more data storage devices, etc. The controller may be connected to any suitable user interface, such as a display, a keyboard, a touchscreen, a mouse, etc.

II. Detection System with Pulsed Illumination

This Section describes an exemplary detection system that uses time multiplexing of excitation light (e.g., pulsed illumination) and/or emission readings to provide "single point" detection of light from fluorescent dyes with overlapping absorption and emission spectra; see FIGS. 4-8. (Fluorescent dyes are compounds including a fluorophore.)

The wavelength regimes in which fluorescence emission occurs may, in some cases, overlap. For example, in some embodiments, there may be two or more fluorophores in the same (or different) droplets, with the excitation spectrum of one fluorophore overlapping the absorption spectrum of another fluorophore (e.g., a first fluorophore might absorb in the blue and emit in the green, while a second fluorophore might absorb in the green and emit in the red). In such cases, it is desirable to separate light detected from the two fluorophores, either by spatially separating the fluorophores (e.g., by spatially separating different droplets containing different fluorophores) and/or by temporally separating the emissions from the fluorophores (e.g., by first exciting and detecting fluorescence from one type of fluorophore, and then exciting and detecting fluorescence from a different type of fluorophore).

Figure 4:
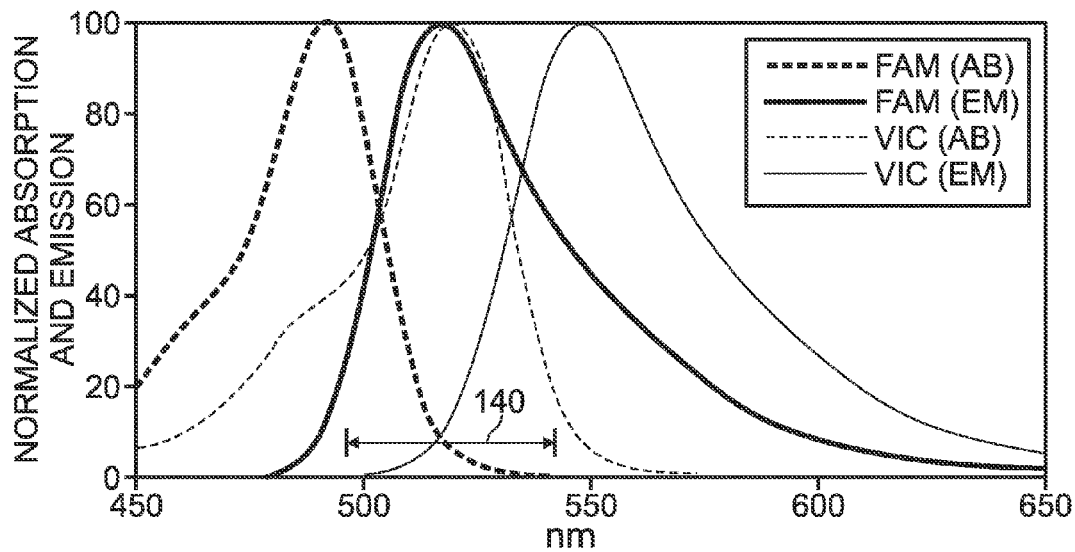
FIG. 4 is a graph of normalized absorption and emission spectra for a pair of exemplary dyes that may be utilized in the detection systems disclosed herein.

FIG. 4 shows a graph illustrating spectral properties of a pair of exemplary dyes with the type of overlap described above. The graph shows normalized absorption and emission spectra for the dyes, which may be utilized in the detection systems disclosed herein. Absorption is used here to represent the excitation spectrum of each dye. The dyes, carboxyfluorescein (FAM) and VIC (Applied Biosystems), are popular as labels for fluorescent oligonucleotide probes, such as TAQMAN probes for real-time PCR assays. Other popular labels that may pose similar problems to FAM dye and VIC dye are TAMRA dye and ROX dye, among others.

FAM and VIC dyes could be used as labels for "two-color" assays in droplets, where light emitted by each label is distinguishable, such as to report the presence or absence of two different targets in each droplet. However, the dyes exhibit a problematic overlap 140 in their spectra: the absorption spectrum of VIC dye and the emission spectrum of FAM dye overlap substantially, and their maxima are nearly at the same wavelength. Overlap 140 extends for about 45 nm and is defined as the waveband where the spectra overlap at 20% or more of their respective maximum values. Accordingly, any light from within a relatively large waveband suitable for VIC dye excitation (i.e., overlap 140) could be detected erroneously as light emission from FAM, thereby giving false or inaccurate results. Also, it may be difficult to select excitation and emission wavelengths for FAM dye and VIC dye that provide sufficient sensitivity to detect VIC emission and sufficient discrimination from FAM emission. In other words, it may be difficult to determine whether strong emission detected with a "VIC" detection configuration results from a droplet producing VIC emission, producing strong FAM emission that is picked up by the VIC detection configuration, or both.

The problem caused by overlap 140 may be eliminated by detecting emitted light from FAM and VIC dyes at respective spatially-shifted examination sites within an examination region of a detection system. In other words, emission from FAM dye could be detected selectively in response to FAM-selective excitation at one examination site and from VIC dye after VIC-selective excitation at the other site. However, separating the examination sites may cause problems correlating fluorescence data from the two sites. In particular, it may be difficult to align or match droplet signals from one site with those of the other site because the relative spacing of droplets and thus the time it takes each droplet to travel between the sites can vary. In other words, droplets can speed up or slow down relative to each other as they travel through an examination region. Stated differently, droplet signals from the sites may not match up with each other with application of only one time offset. Accordingly, two-color droplet assays with spaced examination sites may not be capable of determining how two targets are distributed relative to each other among droplets.

The use of lasers as light sources may overcome some or all of the problems caused by overlap 140. Lasers can provide excitation light of high intensity at a single wavelength, which can promote relatively strong fluorescence emission of a corresponding dye. Because laser excitation may occur at a single wavelength, the laser does not place a substantial limit on the size of the remaining, nonoverlapping range of wavelengths available for detection of emitted light. Also, the strong fluorescence emission stimulated by a laser can enable collection of sufficient emitted light from a relatively narrow waveband, which also helps to avoid any overlap between excitation and emission light. Despite these and other advantages, lasers of sufficient intensity for droplet-based assays can be expensive and in some cases dangerous.

Light-emitting diodes (LEDs) provide a much cheaper and safer light source for fluorescence measurements. However, LEDs would appear to be impractical for many types of fluorescence assays for several reasons. First, LEDs produce light of low intensity compared to lasers, which results in low, and sometimes undetectable, levels of emitted light. The problem can be compounded if much of the emitted light for a dye must be discarded (i.e., filtered out) to minimize or avoid contamination with emitted light from another dye or with excitation light. Second, LEDs emit light over a relatively broad range of wavelengths, such as up to 50 nm or more, while a laser is a single wavelength source. Accordingly, it can be difficult to prevent LED excitation light from contaminating a detection waveband. This problem is greatly exacerbated in a two-color assay, such as with FAM and VIC dyes, for the reasons described above. Third, the spectrum of light produced by an LED is not constant. For example, the wavelength maximum of the LED and/or the shape of its spectral profile may change with temperature, physical changes to the LED itself (such as through aging), or based on the voltage used to energize the LED, among others. In combination, the problems inherent in LEDs as light sources would appear to be insurmountable for a two-color droplet-based assay, particularly with a pair of dyes having spectral overlap 140.

Pulsed illumination, as disclosed herein, may solve some of the problems posed by use of LEDs. Radiation from multiple sources may be configured to intersect with droplets at substantially the same spatial location, for example, by employing a dichroic surface that allows one wavelength range to pass through while reflecting others. In this case, it may be desirable to pulse the excitation sources sequentially so that radiation from only one of the sources arrives at the excitation region at one time. This allows detection of an unambiguous emission signal corresponding to one excitation source at any given instant. Radiation within a particular wavelength regime will arrive at a particular detector. This allows detection of multiple and potentially overlapping emission signals from the same droplet, indicating the presence of multiple different targets in the droplet. The sources may be pulsed sufficiently rapidly that each droplet in an emulsion will be exposed to radiation at least once or multiple times from each source before passing through and out of the excitation region.

The frequency with which different fluorophores are pulsed may be determined by (or at least informed by) the respective lifetimes of the fluorophores. In particular, it may make sense to wait at least a few (e.g., two, three, five, ten, or more) fluorescence lifetimes after exciting one type of fluorophore before exciting (and/or detecting) another type, so that fluorescence from the first type of fluorophore will have sufficiently decayed before exciting (and/or detecting) the other type of fluorophore, to avoid significant signal contamination. In exemplary embodiments, pulse frequencies in the kilohertz and higher range can be achieved with common fluorophores (which can have fluorescence lifetimes in the nanosecond range, among others).

Figure 5:
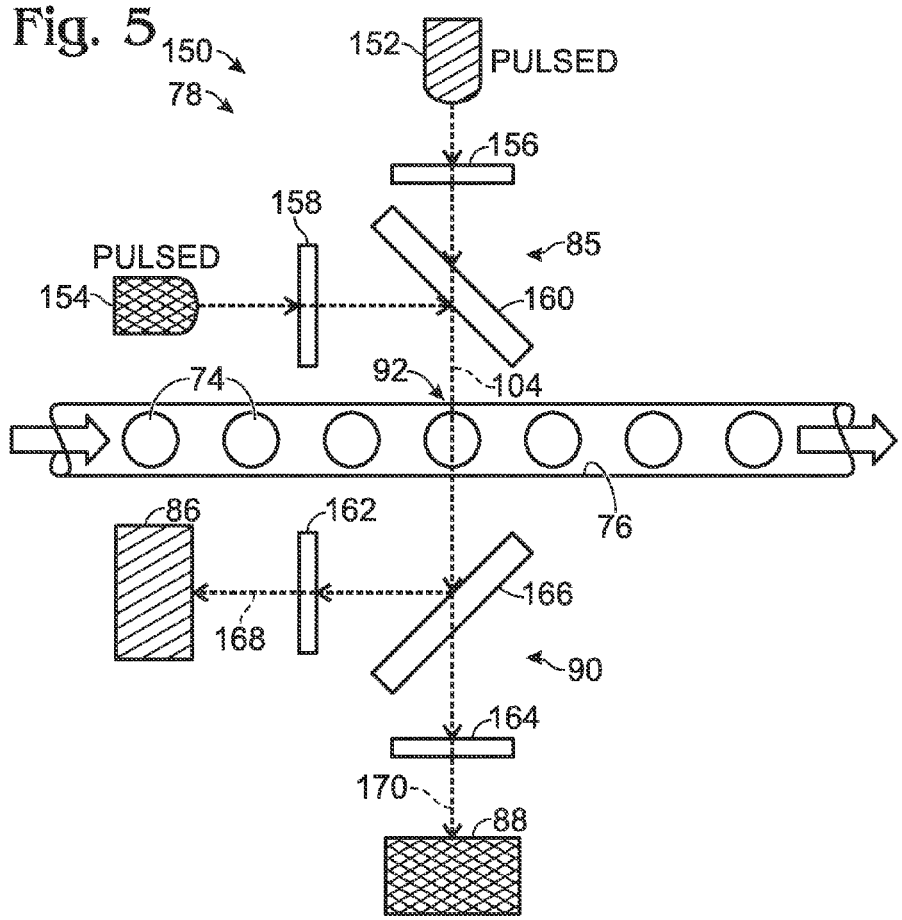
FIG. 5 is a schematic view of selected aspects of another exemplary detection system for droplet-based assays, in accordance with aspects of the present disclosure.

FIG. 5 shows an exemplary detection system 150 that utilizes pulsed illumination, such as from pulsed light sources. In alternative embodiments, illumination optics 85 transmits pulses of light produced from one or more continuous beams generated by continuous light sources. For example, optics 85 may include an electro-optical shutter that blocks a continuous beam of light from a light source between each light pulse. In still other embodiments, the illumination may not be pulsed.

System 150 may offer the same advantage as a system with a pair of light sources at spatially separated examination sites for dye discrimination, without the potential disadvantage of being unable to correlate data from the sites with each other. Furthermore, system 150 enables the use of LEDs as light sources. System 150 may include any suitable combination of the elements, aspects, and features disclosed elsewhere herein for detection systems, such as detection system 120 of FIG. 3.

Detection system 150 may include a pair (or more) of pulsed light sources, such as pulsed source 152 and pulsed source 154. Each light source may emit light of a different (single) wavelength or different wavelength range from the other light source(s). Alternatively, the light sources may emit the same wavelength range of light, but the emitted light may be filtered differently for each source. Illumination assembly 78 of system 150, via pulsed light sources and/or optics 85, may be configured to illuminate examination region 92 in alternation with pulses of light that are spectrally distinct. Spectrally distinct pulses have different wavelength maxima, cover different wavelength ranges, and/or have spectral profiles with distinct shapes, among others.

Detection system 150 can use pulsed sources 152, 154 and detectors 86, 88 as if they form two spatially separated examination sites. The pulses of light from each source may be synchronized with periodic data collection from the detectors. Each source of pulsed illumination may have a corresponding detector, as indicated by the matching hatch patterns: Source 152 is operatively paired with detector 86, and source 154 is operatively paired with detector 88. The examination site defined by source 152 and detector 86 may overlap the examination site defined by source 154 and detector 88, but signals from the source/detector pairs can be distinguished temporally by time-shifted detection and/or data collection from the detectors.

A controller of the system may be operatively connected to the light sources and the detectors (and/or the optics). The controller may generate a separate periodic signal for each source/detector pair. The periodic signal corresponding to a light source/detector pair may result from periodic data collection from the detector, at least predominantly or exclusively during illumination by pulses of light from the light source. Alternatively, or in addition, the periodic signal may result from periodically changing the gain of the detector, synchronized with pulses of light from the light source, or synchronizing pulsed transmission of collected light to the detector with pulses of illumination from the light source. In any event, the periodic signal may represent light detected during illumination of the examination region at least predominantly or exclusively with light emitted by only one of the light sources. Stated differently, the signal may represent light detected by a detector at least predominantly or exclusively during a plurality of spaced time intervals when the examination region is illuminated by a corresponding light source for the detector.

Illumination optics 85 and/or collection optics 90 may help to limit or define wavebands of light used for illumination and detection.

Each light source 152, 154 may be operatively connected to at least one dedicated (or shared) wavelength filter, such as illumination filters 156, 158. The filters may be disposed on dedicated branches of the optical path from each source to channel 76, namely, before beams from the light sources are combined at a combining element 160 (e.g., a dichroic element), such that each filter only affects light from one of the light sources. Illumination filters 156, 158 may function to remove at least one tail formed by the emission spectrum of a light source and/or may improve the ability of each light source to selectively excite a particular dye in the droplets. In other words, the filters may improve the ability of excitation light to discriminate between two or more dyes.

Each detector 86, 88 may be operatively connected to at least one dedicated (or shared) wavelength filter, such as collection filters 162, 164. The filters may be disposed on dedicated branches of the optical path from channel 76 to the detectors. In other words, each filter may be disposed between a beam splitter 166 (e.g., a dichroic filter) and a detector. Collection filters 162, 164 may function to transmit different wavebands of detected light 168, 170 to each detector. Accordingly, the collection filters may be configured to enable each detector to selectively receive emitted light from a particular dye in the droplets. Alternatively, or in addition, the collection filters may be configured, in combination with the illumination filters, to prevent wavelength overlap between incident light 104 and detected light 168, 170. In some embodiments, system 150 also may include a scatter detector to detect light scattered from droplets, which may enable determination of the size of individual droplets passing through the examination region.

FIG. 6 shows a series of graphs 180-184 all representing the same time span and illustrating periodic data that is synchronized with illumination from each of light sources 152, 154. To simplify the presentation, source 152 and source 154 are arbitrarily designated in graphs 180, 182 as "Source 1" and "Source 2," respectively. Also, data representing light detected during pulses of illumination with light from Source 1 is designated as "Signal 1," and data representing light detected during pulses of illumination with light from Source 2, "Signal 2."

Graphs 180, 182 show alternating light pulses 186, 188 of light from Source 1 and Source 2. Each pulse 186, 188 is followed by a pause 190 or 192, with the pulses of light from each respective source occurring during a plurality of spaced time intervals 194. Pulses of illumination of light from each source may be separated by a succession of pauses, generally with the light source emitting (or transmitting) substantially less or no light (e.g., the light source is turned on and off repeatedly, or an electro-optical shutter is opened and closed repeatedly), with each pulse and pause defining one pulse cycle 196. The pulses and pauses for illumination with a light source may be of about the same length or may be of different lengths. Also, the pulse lengths for illumination with each source may be the same or different from each other. The pulses of illumination with the light sources may be at the same frequency (e.g., pulses per second) relative to each other and thus with the same length of pulse cycle, but with a time offset from each other that interleaves pulses of illumination from the light sources. For example, one light source may emit a pulse of light each time the other light source pauses, and vice versa. The time offset between pulses of illumination from the light sources may be about one-half of the duration of one pulse cycle. The interleaved pulses of light from the light sources may exhibit a short time gap where no illumination is occurring (as shown here), may occur in immediate succession with no time gap, or may overlap slightly, among others. Pulsed illumination from each light source may occur at any suitable frequency, such as at least about 100 Hz, 1 kHz, 10 kHz, or 100 kHz, among others. In exemplary embodiments, pulses of illumination with light from each light source more occur at a frequency of about 100 kHz. The pulse cycle may be 10 microseconds, with each pulse and each pause lasting about 5 microseconds. In other embodiments, each pulse may last for less than about 1 millisecond, or less than about 100, 10, or 1 microseconds, among others.

In some cases, the pulse frequency of illumination may be selected to illuminate each droplet with at least one pulse, or two or more pulses, of light from each light source. Accordingly, a suitable pulse frequency may depend on the residence time for a droplet in an examination site and the number of measurements (e.g., signal values) desired for each droplet. The pulse rate may be faster than the time it takes for a droplet to traverse an examination site, such that the droplet is illuminated at least once or multiple times with light from a light source. The pulse rate may be increased for smaller droplets and/or droplets that travel faster. A faster detector may be needed if the pulse rate is increased.

Graph 184 shows how periodic signals 210, 212 generated from light detected by detectors 86, 88 (see FIG. 5) may be synchronized with pulses 186, 188. Periodic Signal 1 (at 210) may be generated from light that is detected by detector 86 at least predominantly or exclusively during pulses of illumination with light from Source 1 (source 152), and periodic Signal 2 (at 212) may be generated from light that is detected by detector 88 at least predominantly or exclusively during pulses of light from Source 2 (source 154).

Graph 184 marks portions of Signals 1 or 2 where each signal is stronger due to the presence of a droplet that is positive for a target (i.e., "Droplet A" for Signal 2 and "Droplet B" for Signal 1). Each droplet is represented by two or three signal values 216 from each of Signal 1 and Signal 2. In some embodiments, more than one signal value 216 may be generated from light detected at different times during each pulse.

The pulse frequency of illumination may be selected to illuminate each droplet with at least one pulse, or two or more pulses, of light from each light source. Accordingly, a suitable pulse frequency may depend on the time of occupancy for a droplet in an examination site and the number of signal values (from different pulses) desired for each droplet. In exemplary embodiments, illumination may be pulsed at 100 kHz for each light source, 1000 droplets per second may pass through the examination site, droplets may be separated from each other on average by two droplet diameters, and about thirty signal values of each signal may be generated for each droplet during thirty pulses of illumination with light from each light source.

FIG. 7 shows an exemplary controller 230 for system 150. Controller 230 may have any of the properties, structures, or features described elsewhere herein, such as for controller 126 of FIG. 3. Controller may include any combination of a gate 232, an amplifier 234, a low-pass frequency filter 236, an analog-to-digital converter 238, and a processor 240, among others. Any of these components may be dedicated to detector 86 or may be shared with detector 88. Amplifier 234 may amplify a signal received from the detector. Filter 236 may remove high frequency components of the signal, to improve the signal-to-noise ratio. Converter 238 may convert an analog signal to a digital signal. Processor 240 may manipulate and/or store the digital signal.

In the configuration shown here, controller 230 is generating a signal value from light 242 detected by only one of the detectors, namely, detector 86 ("DET 1"). Signal generation is indicated by a series of arrows extending between controller components to processor 240. The absence of arrows on the lower line of controller components indicates no signal generation from detector 88.

Light 242 may be detected predominantly from a first dye 244 during a pulse of light from source 152. Controller 230 is not generating a signal value from unwanted light 246 detected by the other detector (detector 88 ("DET 2")), and source 154 is off. Unwanted light 246 may be produced by various mechanisms, such as emission 248 from first dye 244, and emission 250 from a second dye 252 that may absorb light in the pulse from source 152, among others.

Gate 232 is configured to synchronize signal generation from each detector with pulses of illumination with light from the light source corresponding to the detector. The gate may be configured to permit signal generation, and particularly one or more signal values thereof, during each pulse of illumination, while blocking signal generation from the other detector during the pulse. In the present illustration, the gate is blocking signal generation from light detected by detector 88, while permitting signal generation from detector 86. During a subsequent pulse of light from source 154, gate 232, as indicated schematically in phantom at 254, may have the opposite effect on signal generation by the detectors. Gate 232 may be described as a time gate because the gate may operate according to a temporal schedule that corresponds to the schedule of illumination.

The gate may operate on any suitable component(s) to permit and block signal generation. For example, the gate may control operation of the detectors themselves, such as by alternately increasing and decreasing the gain of each detector 86, 88 in substantial synchrony with each pulse of light. In some cases, the gate may be an optical gate, such as an electro-optical shutter, that blocks collected light from reaching the wrong detector (i.e., detector 88 in the configuration of FIG. 7) during a pulse of illumination. Alternatively, the gate may periodically block processing of a substantially continuous signal detected by the detector, in substantial synchrony with illumination pulses from the non-corresponding light source, to convert the continuous signal into a periodic signal. The continuous signal may be analog or digital, and processing may be blocked by gate 232 with the continuous signal in analog or digital form. The gate may, for example, block input of the continuous signal from the detector to amplifier 234, input of the amplified continuous signal to filter 236, or input of the filtered signal to converter 238, among others. In some cases, a continuous signal may be processed digitally by processor 240, such as by selective removal of signal values, to generate a periodic signal. However, passing a continuous signal through analog filter 236, and then converting the continuous signal into a periodic signal by digital processing may be undesirable. The analog filter can degrade the quality of the resulting periodic signal, because the analog filter can smear together portions of the continuous signal, making them difficult to separate when the periodic signal is formed digitally.

FIG. 8 shows yet another exemplary detection system 280 for droplet-based assays. System 280 is similar to detection system 150 of FIG. 5, with the capability of producing pulsed illumination, such as with at least two light sources 152, 154. However, a single detector 282 may be utilized to detect light during illumination with light from each light source. Collection optics of the system may include at least one wavelength filter 284 that selectively excludes one or more wavelength ranges of light. The wavelength filter(s) may be selected to exclude collected light 102 that was emitted by one or both of the light sources, while transmitting collected light emitted by at least a pair of fluorophores in the droplets. Discrimination between signals corresponding to different targets may be based on the ability of the light sources to selectively excite different fluorophores, but generally not based on different emission spectra of the fluorophores, since only a single detector is used.

Detector 282 may create a substantially continuous signal that is representative of light detected during pulsed illumination with light from both of the light sources. The system may use a controller to convert the continuous signal into two or more periodic signals each representing light detected during pulses of illumination with light from a different light source.

III. Detection Unit with a Slit

This Section describes a slit that may be incorporated into the illumination optics and/or collection optics of any of the detection systems disclosed herein; see FIGS. 9 and 10A-C.

Figure 10A:
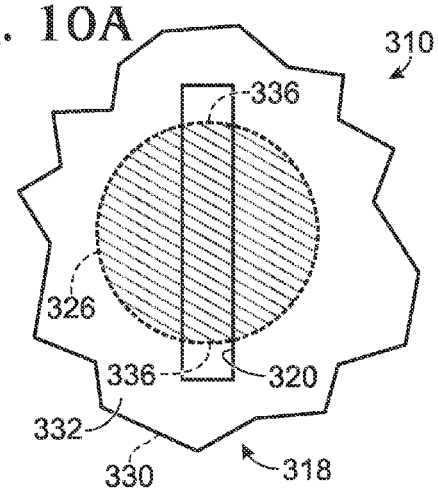
FIG. 10A is a sectional view of the illumination assembly FIG. 9, taken generally along line 10A-10A of FIG. 9 to illustrate an exemplary relationship between a slit and a light beam of the illumination assembly.
Figure 10B:
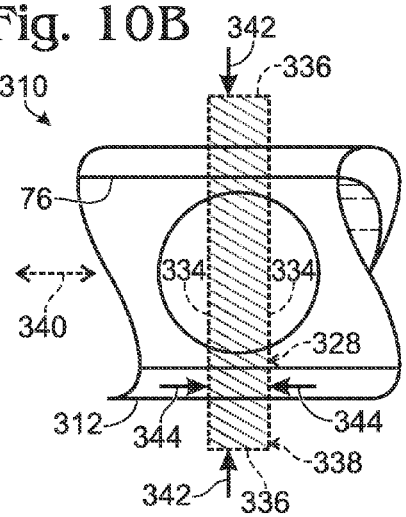
FIG. 10B is a sectional view of the capillary of FIG. 9, taken generally along line 10B-10B of FIG. 9 to illustrate a cross-sectional configuration of a beam shaped by the slit of FIG. 10A.

FIGS. 9, 10A, and 10B shows selected aspects of an exemplary illumination assembly 310 and a tube 312 (e.g., a capillary) that may be included in the detection systems disclosed herein. Tube 312 defines channel 76 in which droplets 74 are illuminated. In exemplary embodiments, tube 312 and channel 76 are cylindrical.

Illumination assembly 310 may include at least one light source 314 and illumination optics 316 that transmit light from the light source to tube 312. The illumination optics may include an aperture element 318 that defines a slit 320. The slit may be disposed before and/or after one or more optical elements 322, 324 on an optical path traveled by light from the light source to channel 76 (see FIG. 9).

A beam 326 of light from light source 314 may be incident on aperture element 318, but only a portion of the beam is permitted to travel through slit 320, to form a shaped beam, namely, a blade 328 of light. In particular, aperture element 318 may include an optically transmissive substrate 330, such as glass, and a blocking layer 332 formed on the substrate. The blocking layer may be substantially opaque, such that it blocks passage of light. In exemplary embodiments, the blocking layer may be formed by selectively removing layer 332, such as by etching. A mask may be formed over layer 332, such as by photolithography, to restrict etching of layer 332 to the position of the slit. The blocking layer may have any suitable composition. In exemplary embodiments, the blocking layer may be composed of gold and chromium. An opposing surface of substrate 330 may include a coating of $MgF_2$.

Blade 328 is elongated in cross section, namely, in a cross-sectional plane taken orthogonal to the direction of travel of the blade of light (as in FIG. 10B). Blade 328 may be described as a planar beam with opposing sides 334 that are at least generally planar. The blade of light may, for example, be formed by illuminating the slit with a substantially collimated beam from a light source of the detection unit. Alternatively, the light source may be imaged onto the slit. In some cases, imaging the light source onto the slit may produce higher intensity illumination of the examination site, everything else being equal, because more light from the light source is incident on the slit (and thus passes through slit) and less light from the light source is incident on and blocked by non-transmissive material flanking the slit.

Slit 320 may have any suitable properties. The slit may be about the same length as, longer than, or shorter than the diameter of beam 326. For example, in shown in FIG. 10A, slit 320 is longer than the beam's diameter, such that opposing ends 336 of blade 328 may not be shaped by the slit (see FIGS. 10A and 10B). The slit may have any suitable width, based on the desired volume of channel 76 to be illuminated, and the amount of magnification or demagnification that will occur between the slit and the channel. For example, blade 328 may travel through at least one lens 324 before the blade illuminates a region of channel 76. Lens 324 may focus an image of the slit onto channel 76 and, optionally, may demagnify the slit's image relative to the slit itself. In exemplary embodiments, slit 320 is about 10 to 200 microns wide, and the image of the slit at the channel is demagnified, such that the thickness of blade 328 at the channel is about 5 to 150 microns, or about 50 to 100 microns, among others.

FIG. 10B shows a cross-sectional area 338 of blade 328 taken at one-half of the distance across channel 76. Blade 328, in cross section, is elongated transversely to a long axis 340 defined by channel 76. The blade may be elongated at least substantially orthogonally to axis 340, namely, within about 20°, 10°, or 5° of orthogonal. A length 342 of the area is substantially greater than its width 344, such as at least about 2, 5, or 10 times as great. Length 342 may be greater than the diameter of channel 76 and/or tube 312. Accordingly, the cross-sectional area of blade 328 at this position along the blade may only partially overlap the channel and/or tube, with the area projecting from one or both opposing sides of the channel and/or tube. A blade in general, and a blade with a cross-sectional length that is greater than the diameter of the channel and/or tube in particular, may offer one or more advantages over illumination with a cylindrical or conical beam of light. These advantages may include a greater tolerance for misalignment of the illumination optics with the channel and/or a decreased tendency for illumination light from two light sources to illuminate non-overlapping regions of the channel.

Blade 328 may illuminate a volume 346 of channel 76 (see FIG. 9). Volume 346 may have a cross sectional shape that corresponds to the cross-sectional shape of channel 76. Accordingly, volume 346 may be substantially disk-shaped if the channel has a substantially cylindrical shape. Volume 346 may have opposing planar sides and a dimension (i.e., width 344 in FIG. 10B), measured parallel to channel axis 340, that is greater than, about the same as, or less than the diameter of a droplet (as shown here). A thinner blade 328 (i.e., a smaller width 344) may permit a higher resolution signal to be created from light detected from volume 346. For example, a blade thinner than the diameter of a droplet may permit collection of more accurate data on droplet size and shape, and better resolution of droplets that are close together in the channel. Also, the use of a slit may permit the use of a lens with a higher numerical aperture to collect the emitted light because illumination is more precise. Alternatively, the use of a slit may permit detection without collection optics.

FIG. 9 shows additional aspects of tube 312. The tube may include a coating or sheath 348 that restricts transmission of light across tube 312. Coating 348 may be selectively removed along a segment 350 of the tube where illumination is conducted. It may be difficult to accurately remove only a short portion of coating 348, so the length of segment 350 may be much greater than the diameter of a droplet. Accordingly, blade 328 may restrict illumination to a short region of segment 350. An exemplary coating is formed of polyimide. In some embodiments, only a short section of coating 348 may be removed (e.g., on the order of the diameter of a droplet or less).

Figure 10C:
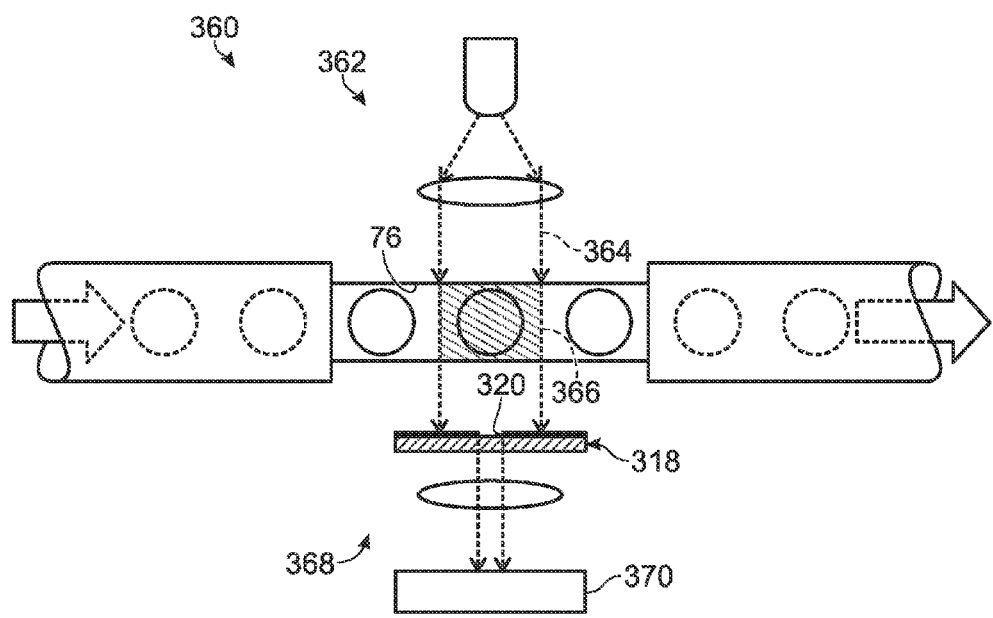
FIG. 10C is a schematic view of selected aspects of an exemplary detection unit and capillary that may be included in the signal detection systems disclosed herein.

FIG. 10C shows selected aspects of another exemplary detection unit 360 that may be included in the signal detection systems disclosed herein. An illumination assembly 362 may illuminate channel 76 with a beam 364 to produce an illuminated volume 366. The illuminated volume may have a dimension, measured along channel 76, that is greater than the diameter of the droplets. Alternatively, the illuminated volume may be produced a blade of light (e.g., see FIGS. 9, 10A, and 10B). In any event, aperture element 318 with slit 320 may be included in collection optics 368 of unit 360. The slit may be oriented substantially orthogonal to a long axis defined by channel 76. The slit may be very close to the channel, such as abutted with a tube or other member that defines the channel. Alternatively, the slit may be disposed in an image plane formed by the collection optics between the channel and a detector 370. A slit included in the collection optics may restrict collection of light to only a portion of an illuminated volume. In some cases, the use of a slit in the collection optics may permit illumination without any illumination optics.

In some embodiments, a slit may be included in the illumination optics, and another slit may be included in the collection optics. The slits may be parallel to each other. The use of a double slit configuration may help to reduce background by more precisely defining illumination and collection volumes of the channel. In some cases, the use slits on both the illumination and collection sides may permit illumination and collection without any other illumination or collection optics.

IV. Droplet Identification with Combined Signals

This Section describes an exemplary approaching to droplet identification by using a combined signal; see FIG. 11.

FIG. 11 shows a flowchart illustrating, with graphs 380-388, an exemplary approach to processing data collected with the detection systems disclosed herein.

Graph 380, which has been described already in relation to FIG. 6, shows a pair of separate signals 210, 212 representative of light detected as droplets in a continuous phase pass through an examination region. Each separate signal includes droplet data 400 for individual droplets interspersed with baseline data 402 for droplet-free regions. One goal is to efficiently identify droplet data for further analysis, free of the baseline data. However, with two or more separate signals (e.g., for two or more targets), the separate signals may not always be in agreement about the location of droplet data, particularly when one or both of the separate signals is close to background. For example, droplet A is identified clearly from Signal 2, but not Signal 1, while the converse is true for droplet B. A signal processing algorithm could examine each signal individually to look for the signature of a droplet, but sometimes a droplet will be identified in one signal but not the other. An approach is need for identifying droplet data that benefits from the information in two or more separate signals representing the same time period of light detection.

Graph 382 illustrates the results of combining the separate signals of graph 380 to form a combined signal 404. In particular, individual signal values 406, 408 representing light detected during the same time interval 410 and from each separate signal 210, 212 may be combined, for each of a succession of time intervals, to produce combined values 412 forming combined signal 404. In some embodiments, signal values from more than two separate signals may be combined. The signal values combined for each time interval may represent light detected during overlapping or nonoverlapping portions of the time interval. For example, in the present illustration, the two separate signals are periodic and temporally offset from each other, and the individual signal values that are combined represent successive, instead of overlapping, portions of the time interval. In other examples, the two (or more) separate signals may be synchronized instead of temporally offset.

Signal values from separate signals may be combined in any suitable fashion. For example, two (or more) signal values for each time interval may be combined to form a linear combination using the following formula:

$$Y = aX_1 + bX_2$$

where Y is a combined value of the combined signal, a and b are constants, and $X_1$ and $X_2$ are corresponding individual signal values from the two separate signals. Additional signal values from other separate signals (e.g., $cX_3$, $dX_4$, etc.) also may be included. The constants may be the same or different. In exemplary embodiments, the constants are at least substantially the same, such that equal proportions of the separate signals are used to generate the combined signal. Accordingly, the combined signal may correspond to an average of separate signals 210, 212.

Individual droplet regions 414 (e.g., peaks or valleys) of the combined signal representing droplets may be identified, as indicated in graph 384. Each droplet region may include a temporal sequence of combined values 412 that collectively produce the signature of a droplet. Droplet identification may be performed by processing the combined signal with any suitable algorithm to look for a droplet signature. Exemplary droplet identification algorithms may be based on one or more predefined conditions corresponding to an acceptable range for the height (or depth), width, smoothness, and/or monotonicity of a peak 415 (or valley) formed by the combined signal.

Signal values corresponding to each droplet region 414, from each separate signal, indicated at 416, 418, may be processed selectively relative to other signal values, as indicated in graphs 386, 388. This selective processing may ignore any signal values, not shown in the graphs, disposed outside of identified droplet regions. The selective processing may determine whether a target represented by each separate signal is present or absent in droplets corresponding to the droplet regions.

V. Optical Layout for a Detection Unit

Figure 12:
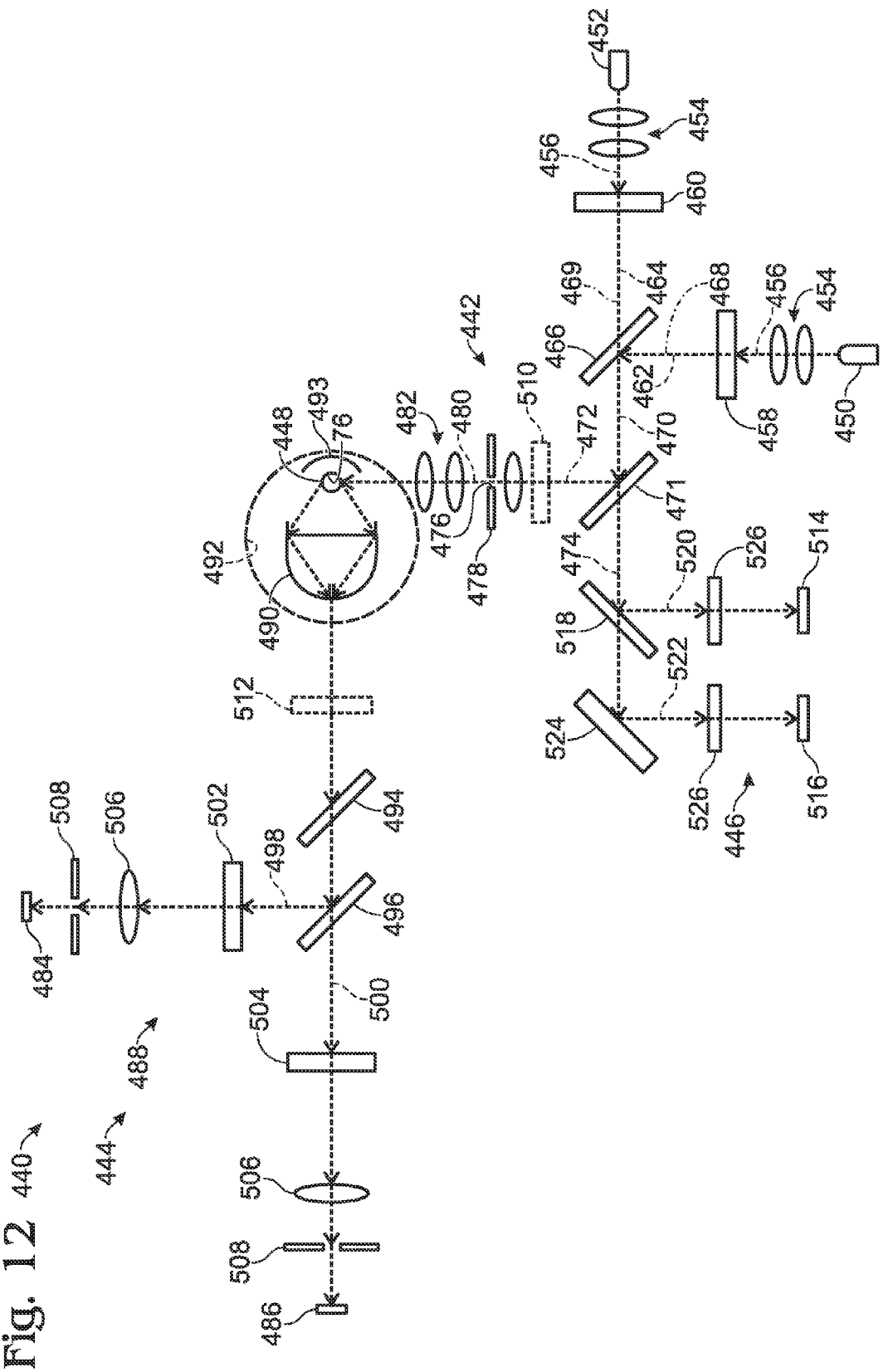
FIG. 12 is a view of an optical layout of an exemplary detection unit for the detection systems disclosed herein, such as the system of FIG. 5, in accordance with aspects of the present disclosure.
Figure 13:
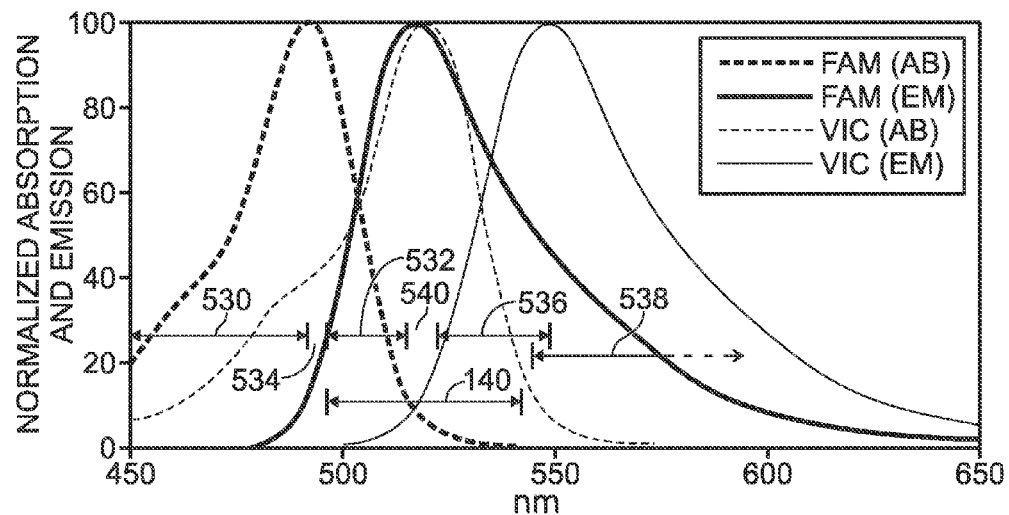
FIG. 13 is the graph of FIG. 4 supplemented with exemplary wavebands of illumination and detection that may be suitable for the dyes of FIG. 4 used in the detection system of FIG. 5 equipped with the detection unit of FIG. 12, in accordance with aspects of the present disclosure.

This Section describes an exemplary detection unit 440, particularly an exemplary optical layout thereof, for the detection systems disclosed herein; see FIGS. 12 and 13. Detection unit 440 may, for example, be incorporated into detection system 150 (see FIG. 5).

Detection unit 440 may include an illumination assembly 442, a collection assembly 444, and a monitoring assembly 446, among others. Illumination assembly 442 may illuminate a capillary 448 defining channel 76. The collection assembly may collect and detect light received from channel 76, particularly emitted light.

The illumination assembly may be equipped with a blue LED 450 and a cyan LED 452 that emit light at about 440-520 nm (maximum at 480-485 nm) and 470-550 nm (maximum at 505-510 nm), respectively. The LEDs may produce a luminous flux of about 10 to 200 lumens, among others, at a drive current of about 300 to 1000 mA. Each LED may be configured to be pulsed at any suitable frequency, such as about 100 kHz each, with the pulses of the light sources interleaved with each other.

Light from each LED 450, 452 may travel through a lens doublet 454 that collimates light emitted by the LED, to form a collimated beam 456. Each collimated beam may be filtered through a respective filter, namely, wavelength filter 458 or 460. Filter 458 may be a short-pass filter that permits passage of light of 485 nm or less, and filter 460 may be a band-pass filter that permits passage of light of 497-518 nm, to produce filtered beams 462, 464. The filtered beams may be combined at a dichroic element 466 oriented at 45 degrees to optical axes 468, 469 extending to the beams from the LEDs. Dichroic element 466 may have a nominal reflection cut off of about 495 nm, such that light from blue LED 450 and cyan LED 452 are combined efficiently. In some embodiments, dichroic element 466 may be rotated 90 degrees about axis 469. Also, the optical axis of filtered blue beam 462 may extend to the rotated dichroic element from back to front in the current view, with blue LED 450 positioned behind dichroic element 466 in the current view.

In any event, filtered beams from the LEDs may be combined by dichroic element 466, to produce a combined beam 470 that is split by a dichroic beam splitter 471, to form a main beam 472 and a sampling beam 474. A majority of the light (e.g., 95%) may form the main beam and a minority of the light (e.g., 5%) may form the sampling beam. The sampling beam will be described further below in relation to monitoring assembly 446. Main beam 472 may travel through a slit 476 defined by an aperture element 478 (e.g., see aperture element 318 of FIGS. 9 and 10A-C), to form a blade of light 480, which may be focused onto capillary 448 by a pair of spaced lenses 482. The blade of light may define a plane that that is substantially orthogonal to the long axis of the capillary 448 where the blade of light intersects the capillary.

Collection assembly 444 gathers and detects light received from capillary 448. The optical axis of the collected light may be substantially orthogonal to both the long axis of the capillary and to the axis of illumination defined by the illumination light of blade 480. The collection assembly 444 may, for example, be equipped with a pair of photomultiplier tubes (PMTs) 484, 486 that serve as detectors of light collected from the capillary by collection optics 488. Optics 488 receives light for the two detectors from the capillary along a shared optical axis that branches into a pair of optical axes extending to the respective PMTs.

The shared optical axis extending from the capillary may include an aspheric lens 490 disposed close to the capillary. Lens 490 may provide a high numerical aperture (10 mm diameter, 0.625 NA) for efficient collection of emitted light. Also, the examination site of the capillary that is illuminated may be substantially enclosed by a chamber 492, which permits entry of incident illumination light and exit of emitted light via the aspheric lens, but otherwise blocks light. The chamber may be lined with a light-absorbing material (i.e., a blackened chamber) and may minimize or eliminate the occurrence of objects or edges, to minimize scattered and reflected light. The chamber also may contain at least one mirror 493 that reflects emitted light toward aspheric lens. In other words, the mirror may help collect light that is emitted away from the aspheric lens, to improve the efficiency which emitted light is detected. The mirror may, for example, be an elliptical mirror. In some cases, the examination site may be disposed at least generally between the mirror (or at least a region thereof) and a collection optical element (e.g., aspheric lens 490) and/or a detector (e.g., if no collection optics are used).

The collected light from aspheric lens 490 may travel through a clean-up dichroic element 494, which rejects light of less than 500 nm, to remove residual excitation light, if any, from the LEDs, particularly light emitted by blue LED 450. Light transmitted through dichroic element 494 next encounters dichroic beam splitter 496, which splits the light to form a reflected split beam portion 498 of less than about 550 nm and a transmitted split beam portion 500 of greater than about 550 nm. Split beam portion 498 is transmitted to PMT 484, and split beam portion 500 to PMT 486. Each beam portion may travel through one or more wavelength filters, such as respective filters 502 or 504, at least one lens 506, and an optional aperture element 508 before reaching the respective PMT. Filter 502 may be a long-pass filter that rejects light of less than about 540 nm. Filter 504 may be a band-pass filter that rejects light off less than about 520 nm and of greater than about 555 nm.

The filters used in the illumination optics and the collection optics may effectively prevent all excitation light from reaching the detectors. However, contamination of detected light with excitation light also or alternatively may be reduced or eliminated by the use of polarization filters that are cross-polarized with respect to each other. Illumination light from each light source may be polarized on the optical path to the capillary, after the beams are combined, with a first polarization filter 510 (an illumination filter), to form a polarized light beam from the light sources. Collected light may be transmitted through a second polarization filter 512 (a collection filter) before the collected light beam has been split. Accordingly, second filter 512 will block light polarized by first filter 510 because such light is polarized in the cross plane that is blocked by the second filter. In this way, illumination/excitation light that is collected can be blocked by the second polarization filter from reaching either detector. This arrangement of filters may be particularly suitable with a pair of dyes, such as VIC and FAM dyes, where one of the dyes (e.g., VIC dye) has an excitation spectrum that overlaps the emission spectrum of the other dye. Also, or alternatively, this filter arrangement may reduce channel cross-talk. Filters 510 and 512 may be absorptive linear polarizers that polarize light in respective orthogonal planes. Light emitted from capillary 448 generally is unpolarized, so a substantial part of the emitted light (e.g., about half) may be capable of traveling through polarization filter 512.

Monitoring assembly 446 may monitor the illumination intensity of illumination light from each LED 450, 452. The monitoring assembly may be arranged as part of a feedback loop with a controller and LEDs 450, 452 to maintain the illumination intensity at the capillary substantially constant. Sampling beam 474 is received by assembly 446 from beam splitter 470 after the waveband of capillary illumination by each LED has been determined by respective filters 458, 460. Accordingly, any intensity change for each waveband that is produced by an overall increase or decrease in light output by an LED, in addition to any intensity change produced by a shift or other alteration in the spectral profile of the corresponding LED, can be measured by assembly 446.

Monitoring assembly 446 may include a corresponding sensor 514 or 516 for each light source. The sensor may, for example, be a photodiode. Sampling beam 474 may be split by a dichroic beam splitter 518, which may have at least substantially the same reflection properties as dichroic element 466 (e.g., a nominal reflection cut-off of 495 nm). In other words, beam splitter 518 acts to reverse the effect of dichroic combining element 466. Beam splitter 518 thus may produce respective blue and green beam portions 520, 522 corresponding respectively to LEDs 450, 452. Green beam portion 522 may be reflected by a mirror 524 toward sensor 516. Each beam portion may be passed through a diffuser 526 before reaching the respective sensor 514 or 516.

FIG. 13 shows the graph of FIG. 4 supplemented with exemplary wavebands of illumination and detection that may be suitable for the dyes of FIG. 4, namely FAM dye and VIC dye, in the detection system of FIG. 5 equipped with detection unit 440 of FIG. 12. One of the light sources, namely, blue LED 450, may illuminate capillary 448 with a waveband 530 of less about 485 nm. Waveband 530 may or may not have a defined shorter wavelength boundary. The other light source, namely, cyan LED 452 may illuminate capillary 448 with a waveband 532 of about 495-515 nm. Accordingly, there may be (or may not) be overlap between the wavebands. In some cases, a gap 534 may be formed between illumination wavebands 530, 532. Gap 534 may, for example, be at least about 2, 5, or 10 nm, among others. In some cases, one or both of the light sources (e.g., a laser) may emit light of a single wavelength instead of a range of wavelengths. In some cases, a single light source may produce excitation light for both dyes. In any event, light from waveband 530 is selectively absorbed by one of the dyes (FAM dye) and light from waveband 532 is selectively absorbed by the other dye (VIC dye). Accordingly, LED 450 selectively excites FAM dye, and LED 452 selectively excites VIC dye.

Light may be collected in detection wavebands 536, 538. The detection wavebands may or may not overlap. If there is overlap, the amount of overlap may be about 0-20 or 0-10 nm, among others. Detection waveband 536 is selective for emission from one of the dyes (FAM dye), and detection waveband 538 for emission from the other dye (VIC dye). Accordingly, detection waveband 536 corresponds to illumination waveband 530, blue LED 450, and FAM dye, and detection waveband 538 corresponds to illumination waveband 532, cyan LED 452, and VIC dye.

Illumination waveband 532 and detection waveband 536 represent different dyes. These wavebands potentially could overlap if light is detected from detection waveband 536 only when cyan LED 452 is off, e.g., by using interleaved pulses of light as described above in Section II. However, the detector for detection waveband 536 may become saturated by the light from illumination waveband 532, during a pulse from LED 452. The pulse may render the detector incapable of accurately measuring light during the next pulse with the other light source, after LED 452 is turned off, because the recovery time for the detector may be much longer than the pulse duration. Therefore, it may be desirable to separate illumination waveband 532 from detection waveband 536. Alternately, or in addition, it may be desirable to gate off a detector (e.g., detector 486) for waveband 536 during the period of illumination with waveband 532. This can, for example, be accomplished by decreasing the dynode voltage of a PMT detector or the bias voltage on an APD (avalanche photodiode) detector, or using an electro-optical shutter to block light from reaching the detector, among others.

An exemplary strategy for dividing up overlap 140, in a balanced manner, between illumination waveband 532 and detection waveband 536 is shown in the graph. A shorter wavelength segment (i.e., waveband 532) may be dedicated to illumination, and a nonoverlapping, longer wavelength segment (i.e., waveband 536) may be dedicated to detection. Segments of about the same size (within about 50% of each other in length) from overlap 140 may be assigned to illumination and detection. Wavebands 532 and 536 may be separated by a gap 540 of at least about 2, 5, or 10 nm, to prevent any excitation light from reaching the detector. Gap 540 may be positioned near (e.g., within about 10 nm or 20 nm) a maximum value of the absorption spectrum of one of the dyes and/or a maximum value of the emission spectrum of the other dye.

VI. Detection System with Spaced Examination Sites

Figure 14:
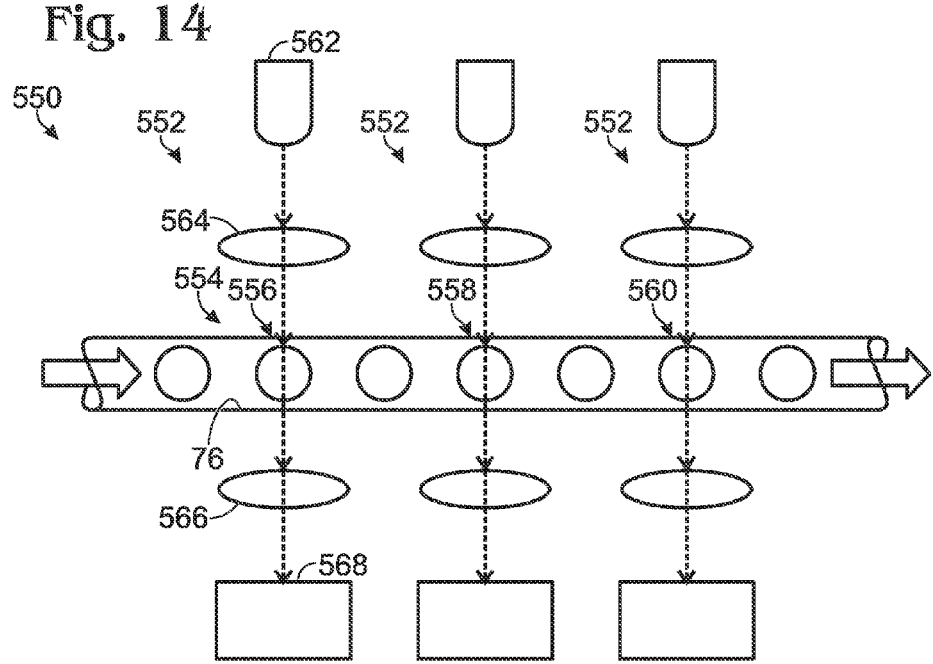
FIG. 14 is a schematic view of selected aspects of still yet another exemplary detection system for droplet-based assays, with the system including a series of detection units arranged to define a discontinuous examination region formed of spaced examination sites disposed along a channel, in accordance with aspects of the present disclosure.
Figure 15:
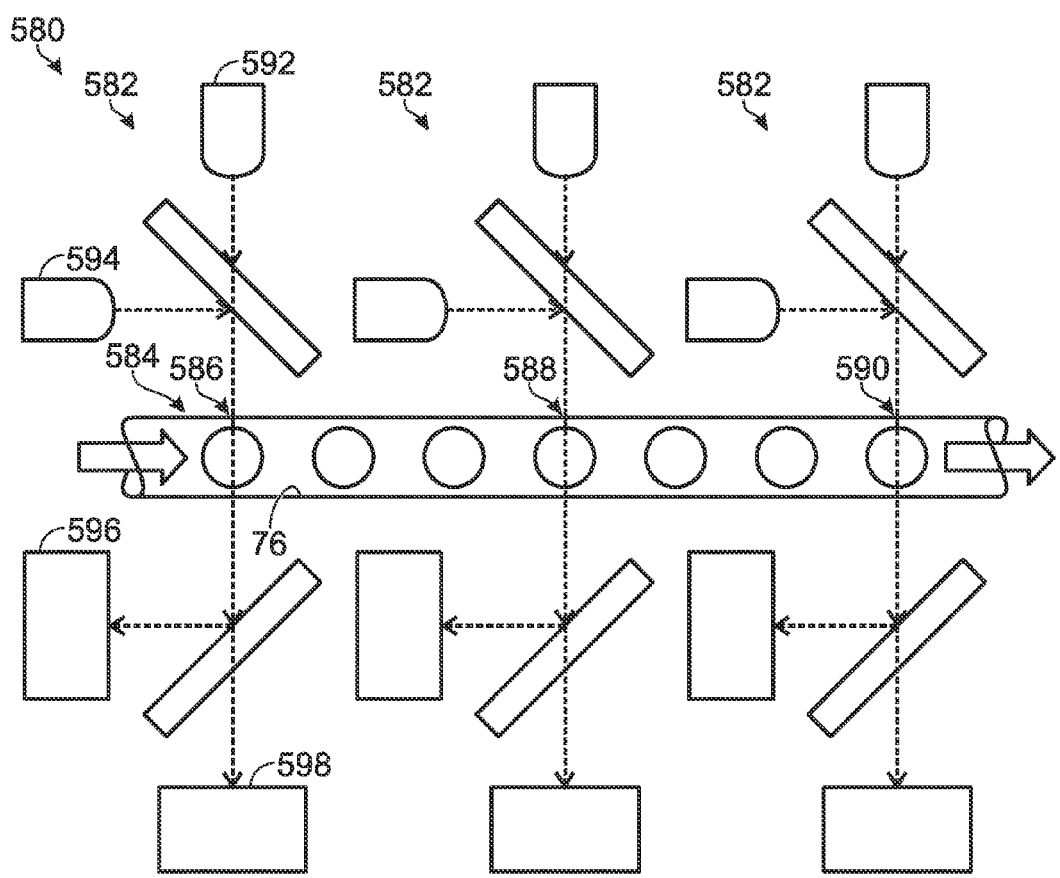
FIG. 15 is a schematic view of selected aspects of another exemplary detection system for droplet-based assays, with the system including multiple detection units from the system of FIG. 5 arranged to define a discontinuous examination region formed of spaced, multi-color examination sites disposed along a channel, in accordance with aspects of the present disclosure.
Figure 16:
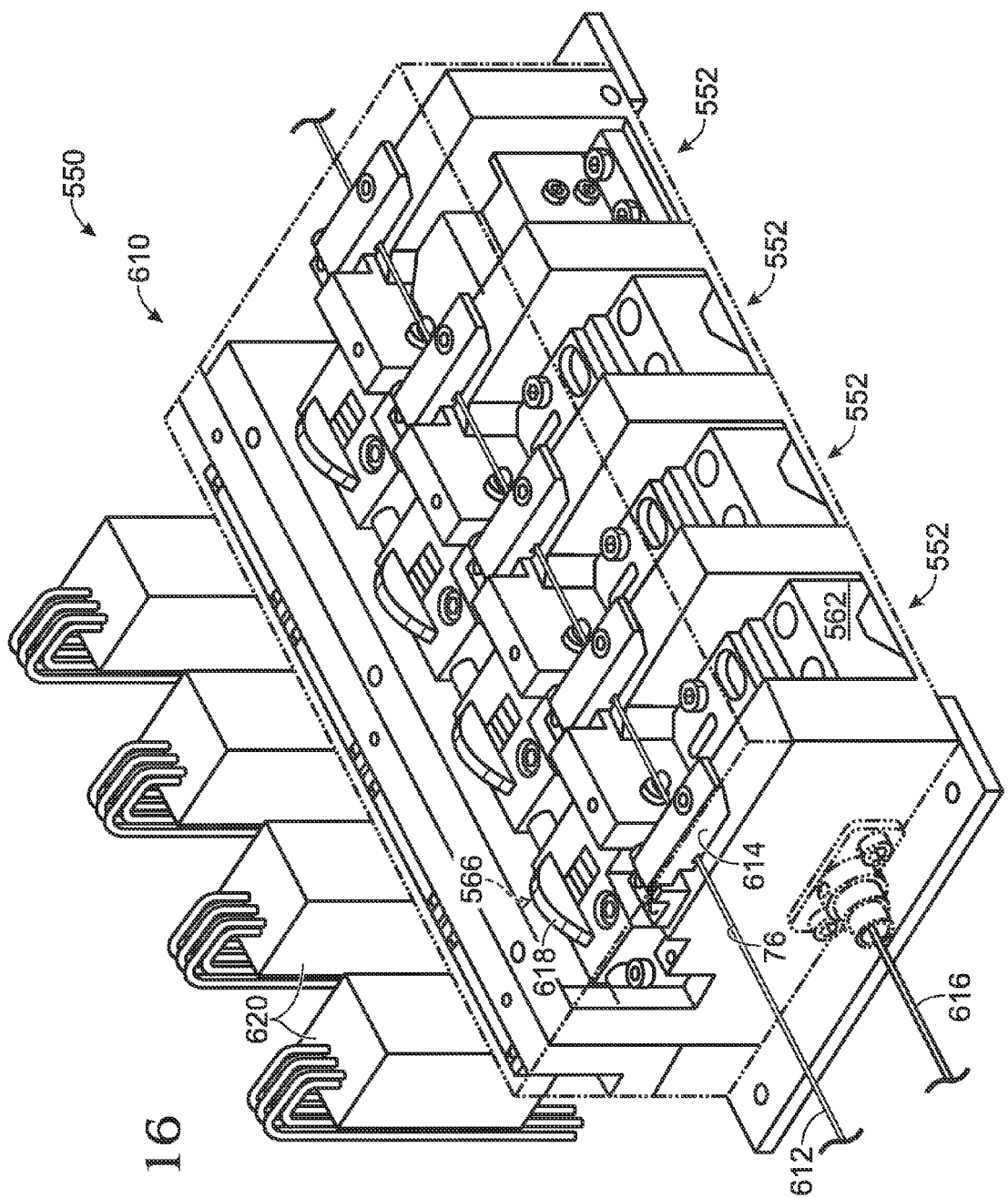
FIG. 16 a view of selected aspects of an embodiment of a detection system constructed according the system configuration of FIG. 14, in accordance with aspects of the present disclosure.

This Section describes exemplary detection systems that define spaced examination sites with spatially separated excitation/emission volumes; see FIGS. 14-16.

In some system embodiments, radiation from multiple excitation sources may be spatially shifted, i.e., may intersect with droplets at substantially different spatial locations. In this case, the excitation sources need not be pulsed or otherwise alternating, since radiation from only one source reaches any particular droplet at a given time. As in the case of systems with a single common excitation region or point, systems having multiple spatially shifted excitation regions may use a beam splitter and/or filters in conjunction with multiple detectors to distinguish between droplet emission signals, or may use a single detector capable of distinguishing between emission spectra resulting from excitation of different target molecules.

FIG. 14 shows an exemplary detection system 550 with spatially shifted examination sites for droplet-based assays. System is equipped with multiple detection units 552 arranged to define a discontinuous examination region 554 formed of spaced examination sites 556-560 disposed along channel 76.

The examination sites may have any suitable spacing from one another (e.g., less than about 5 cm, 1 cm, or 1 mm, or less than about 100, 50, 25, or 10 droplet or channel diameters, among others). It may be desirable to place the examination sites as close together as possible because closer examination sites make correlating data detected from different examination sites less problematic. There is less time for droplets to change their relative separations from one another in the flow stream as such droplets travel between examination sites. In some configurations, a series of examination sites may be close enough to one another that each droplet travels through all of the sites before the next droplet enters the examination region. With sites this close, there is no problem syncing droplet data collected from the examination sites.

Each detection unit 552 may include at least one light source 562, illumination optics 564, collection optics 566, and a detector 568. The detection units, relative to one another, may provide different wavelengths or wavebands of illumination light and/or may detect different wavelengths or wavebands of collected light.

FIG. 15 shows yet another exemplary detection system 580 for droplet-based assays. System 580 includes multiple detection units 582 arranged to define a discontinuous examination region 584 formed of spaced examination sites 586-590 disposed along channel 76. Each detection unit may include at least one or at least a pair of light sources 592, 594 and at least one or at least a pair of detectors 596, 598. In some embodiments, one or more of the detection units may incorporate any combination of features disclosed above for detection system 150 or 280 (FIGS. 4-8), illumination assembly 310 (FIGS. 9 and 10A-C), and/or detection unit 440 (FIG. 12), such as pulsed illumination and generation of a periodic signal corresponding to pulses of illumination, a slit to shape and/or selectively block a light beam, use of a combined signal to identify droplets, balanced division of a region of excitation/emission overlap for dyes to an illumination waveband for one dye and a detection waveband for the other dye, and/or closed-loop monitoring of illumination intensities, among others.

FIG. 16 shows an embodiment 610 of detection system 550. A capillary 612 defining channel 76 extends through each detection unit 552. The capillary is clamped in place by brackets 614. Each light source 562 includes an LED. An alternative light source or light collector, an optical fiber 616, extends through the detection units. Collection optics 566 of each unit 552 may include a filter 618, which may be interchangeable readily by a user. Light may be detected by photomultiplier tubes 620.

VII. Selected Embodiments

This section describes additional aspects and features of detection systems for droplet-based assays, presented without limitation as a series of numbered paragraphs. Each of these paragraphs can be combined with one or more other paragraphs, and/or with disclosure from elsewhere in this application, in any suitable manner. Some of the paragraphs below expressly refer to and further limit other paragraphs, providing without limitation examples of some of the suitable combinations.

1. A method of detection for droplets, comprising: (A) illuminating an examination region of a channel with first pulses of light interleaved with second pulses of light as droplets pass through the examination region, the first pulses being spectrally distinct from the second pulses; and (B) collecting data representing light detected during illumination of the examination region with the first pulses and the second pulses.

2. The method of paragraph 1, wherein the first pulses define a first range of wavelengths of light and the second pulses define a second range of wavelengths of light, and wherein the first range is different from the second range.

3. The method of paragraph 1, wherein only the first pulses are produced by a single wavelength of light, or both the first pulses and the second pulses are produced by respective single wavelengths of light.

4. The method of any of paragraphs 1 to 3, wherein the first pulses are produced by a pulsed light source.

5. The method of any of paragraphs 1 to 4, wherein the first pulses and the second pulses are produced by respective pulsed light sources.

6. The method of paragraph 1, wherein the first pulses, the second pulses, or both the first and second pulses are produced by at least one continuous light beam that is transmitted intermittently to the examination region.

7. The method of paragraph 1, wherein the first pulses and the second pulses include light emitted by at least one LED.

8. The method of paragraph 7, wherein the first pulses and the second pulses are emitted by respective pulsed LEDs.

9. The method of paragraph 1, wherein overlapping volumes of the examination region are illuminated by the first pulses and the second pulses.

10. The method of paragraph 1, further comprising a step of detecting light from overlapping volumes of the examination region during the first pulses and the second pulses.

11. The method of paragraph 1, wherein each droplet is illuminated with at least one first pulse and at least one second pulse.

12. The method of paragraph 11, wherein each droplet is illuminated with multiple first pulses and multiple second pulses.

13. The method of paragraph 1, wherein each droplet is illuminated with a beam of light that is narrower than a diameter of the droplets.

14. The method of paragraph 1, wherein the first pulses and second pulses contain light emitted by respective first and second light sources, further comprising a step of passing the light emitted by the first and second sources through a slit before such light illuminates the examination region.

15. The method of paragraph 1, wherein the step of collecting data includes a step of generating a first signal and a second signal representing light detected during illumination of the examination region with the first pulses and the second pulses, respectively.

16. The method of paragraph 15, wherein the droplets include a first dye and a second dye, wherein the first signal is generated from a first detection configuration and the second signal is generated from a second detection configuration, and wherein the first detection configuration has a different relative sensitivity to the first and second dyes than the second detection configuration.

17. The method of paragraph 15, further comprising a step of detecting light from the examination region with a first detector and a second detector, and wherein the first signal represents light detected at least predominantly by the first detector and the second signal represents light detected at least predominantly by the second detector.

18. The method of paragraph 17, wherein each detector detects light during the first pulses and the second pulses.

19. The method of paragraph 17, wherein a gain of each detector is adjusted over time according to whether a first pulse or a second pulse is illuminating the examination region of the channel.

20. The method of paragraph 15, wherein the first signal and the second signal are periodic signals.

21. The method of paragraph 1, wherein the data represents light detected with a same detector during illumination of the examination region with the first pulses and the second pulses.

22. The method of paragraph 1, further comprising a step of detecting light from the examination region during the first pulses and the second pulses, wherein the step of detecting light creates a first signal and a second signal, and wherein the step of collecting data includes a step of periodically gating the first signal and the second signal in correspondence with the first pulses and the second pulses, respectively.

23. The method of paragraph 1, wherein the step of illuminating includes a step of intersecting the channel with a beam of light having a cross section that is elongated transversely to a long axis defined by the channel.

24. The method of paragraph 1, wherein the step of illuminating includes a step of illuminating a disk-shaped volume of the channel.

25. The method of paragraph 1, wherein the step of illuminating includes a step of illuminating the examination region of the channel with third pulses of light that are spectrally distinct from the first pulses and the second pulses.

26. A method of detection for droplets, comprising: (A) illuminating an examination region of a channel alternately with pulses of light emitted by a first light source and a second light source as droplets pass through the examination region; (B) detecting light from the examination region illuminated by the pulses of light; and (C) generating a first signal and a second signal, the first signal representing light detected at least predominantly when the first region is illuminated with pulses of light from the first light source and the second signal representing light detected at least predominantly when the second region is illuminated with pulses of light from the second light source.

27. The method of paragraph 26, further comprising a step of estimating a concentration of a first target and a second target in the droplets based on the first signal and the second signal.

28. The method of paragraph 26, further comprising a step of determining whether an amplification reaction occurred in individual droplets.

29. A system for detection for droplet-based assays, comprising: (A) a channel; (B) an illumination assembly configured to illuminate an examination region of the channel with first pulses of light interleaved with second pulses of light as droplets pass through the examination region, the first pulses being spectrally distinct from the second pulses; (C) one or more detectors configured to detect light from the examination region; and (D) a controller that collects data representing light detected during illumination of the examination region with the first pulses and the second pulses.

30. The system of paragraph 29, wherein the first pulses define a first range of wavelengths of light and the second pulses define a second range of wavelengths of light, and wherein the first range is different from the second range.

31. The system of paragraph 29, wherein only the first pulses are produced by a single wavelength of light, or both the first pulses and the second pulses are produced by respective single wavelengths of light.

32. The system of paragraph 29, wherein the illumination assembly includes at least one pulsed light source.

33. The system of paragraph 29, wherein illumination assembly include a pair of pulsed LEDs.

34. The system of paragraph 29, wherein the illumination assembly includes at least one continuous light source configured to emit a beam of light that is transmitted intermittently to the examination region.

35. The system of paragraph 29, wherein the first pulses and the second pulses are configured to illuminate overlapping volumes of the examination region.

36. The system of paragraph 29, wherein the one or more detectors are configured to detect light from overlapping volumes of the examination region during the first pulses and the second pulses.

37. The system of paragraph 29, wherein the illumination assembly is configured to illuminate the examination region with a beam of light that is elongated in cross section and in a direction transverse to a long axis defined by the channel.

38. The system of paragraph 29, wherein the illumination assembly includes a least one slit through which light travels before illuminating the examination region.

39. The system of paragraph 29, wherein the controller is configured to generate a first signal and a second signal representing light detected during illumination of the examination region with the first pulses and the second pulses, respectively.

40. The system of paragraph 39, wherein the one or more detectors include a first detector and a second detector, and wherein the first signal represents light detected at least predominantly by the first detector and the second signal represents light detected at least predominantly by the second detector.

41. The system of paragraph 40, wherein each detector is configured to detect light during the first pulses and the second pulses.

42. The system of paragraph 39, wherein the first signal and the second signal are periodic signals.

43. The system of paragraph 29, wherein the controller is configured to adjust a gain of each detector over time according to whether a first pulse or a second pulse is illuminating the examination region of the channel.

44. The system of paragraph 29, wherein the one or more detectors create a first signal and a second signal that are each at least substantially continuous, and wherein the controller is configured to periodically gate the first signal and the second signal in correspondence with the first pulses and the second pulses, respectively, to make the signals periodic.

45. The system of paragraph 29, wherein the illumination assembly forms a beam of light having a cross section that is elongated transversely to a long axis defined by the channel.

46. The system of paragraph 29, wherein the illumination assembly is configured to illuminate a disk-shaped volume of the channel.

47. The system of paragraph 29, wherein the illumination assembly includes a first light source and a second light source, further comprising at least one pump configured to drive the droplets through the examination region as the light sources illuminate overlapping volumes of the channel.

48. A system for detection in droplet-based assays, comprising: (A) a channel; (B) an illumination assembly configured to produce a beam of light that illuminates an examination region of the channel as droplets pass through such region; (C) a detector configured to detect light received from the examination region; and (D) a controller that collects data representing light detected by the detector, wherein the beam of light is elongated in cross section where the beam intersects the channel.

49. The system of paragraph 48, wherein the illumination assembly includes a light source and a slit, and wherein light emitted by the light source travels through the slit before reaching the examination region.

50. The system of paragraph 48, wherein the beam of light is elongated in cross section in a direction transverse to a long axis defined by the channel.

51. The system of paragraph 48, wherein a cross section of the beam, at a position halfway across the channel, extends outside opposing surfaces of the channel.

52. The system of paragraph 51, where the channel is defined by a tube, and wherein a cross section of the beam, at a position halfway across the channel, is longer than a diameter of the tube.

53. The system of paragraph 52, wherein the cross section at a position halfway across the channel has opposing ends that do not intersect the tube.

54. The system of paragraph 48, wherein the beam of light illuminates a disk-shaped volume of the channel.

55. The system of paragraph 48, wherein the beam of light has opposing planar sides.

56. The system of paragraph 48, wherein the beam of light has a dimension measured parallel to a long axis of the channel where the channel and the beam intersect, and wherein the dimension is less than a diameter of the channel.

57. A system for detection in droplet-based assays, comprising: (A) a channel; (B) a light source that illuminates an examination region of the channel as droplets pass through such region; (C) a detector configured to detect light received from the examination region; and (D) a controller that collects data representing light detected by the detector, wherein light emitted by the light source travels through at least one slit between the light source and the detector.

58. The system of paragraph 57, wherein the at least one slit includes a slit disposed on an optical path from the light source to the examination region.

59. The system of paragraph 57, wherein the at least one slit includes a slit disposed between collection optics and the channel.

60. A method of detection for droplets, comprising: (A) illuminating an examination region of a channel with a beam of light that is elongated in cross section; and (B) collecting data representing light detected over time from the region as a plurality of droplets pass through the examination region.

61. The method of paragraph 60, wherein the step of illuminating includes a step of transmitting light through a slit disposed on an optical path between a light source and the examination region.

62. The method of paragraph 60, wherein a disk-shaped volume of the examination region is illuminated.

63. The method of paragraph 60, wherein the beam of light is elongated in cross section in a direction that is transverse to a long axis defined by the channel.

64. The method of paragraph 60, wherein the step of illuminating includes a step of illuminating droplets with a beam of light that is thinner than a diameter of the droplets.

65. A method of detection for droplet-based assays, comprising: (A) generating at least two separate signals each representing light detected with a different detection configuration during a series of time intervals from a stream of fluid carrying droplets; (B) combining the at least two separate signals to form a combined signal; and (C) processing the combined signal to identify time intervals that correspond to droplets.

66. The method of paragraph 65, wherein the step of combining includes a step of forming a linear combination of values from the separate signals for individual time intervals.

67. The method of paragraph 66, wherein the step of forming a linear combination includes a step of forming a linear combination of the values in equal proportions.

68. The method of paragraph 65, wherein the step of combining is performed with the at least two signals in digital form.

69. The method of paragraph 65, wherein the step of combining is performed at least in part as the at least two signals are being generated.

70. The method of paragraph 65, wherein the step of combining includes a step of combining values from the separate signals for individual time intervals, and wherein each value that is combined for a given time interval represents light detected during a different part of the given time interval.

71. The method of paragraph 70, wherein each value that is combined for a given time interval represents light detected during nonoverlapping portions of the given time interval.

72. The method of paragraph 65, wherein the step of combining includes a step of combining values from the separate signals for individual time intervals, and wherein each value that is combined for a given time interval represents light detected during a same part or all of the given time interval.

73. The method of paragraph 65, wherein the separate signals include a first signal and a second signal representing light detected from a region of a channel holding the stream of fluid during illumination of the region with alternating pulses of light from a first light source and a second light source.

74. The method of paragraph 73, wherein the first signal at least predominantly represents light detected by a first detector during pulses from the first light source, and wherein the second signal at least predominantly represents light detected by a second detector during pulses from the second light source.

75. The method of paragraph 65, wherein each different dye includes a fluorophore.

76. A method of detection for droplet-based assays, comprising: (A) generating at least two separate signals each representing a respective different wavelength or waveband of light detected during a series of time intervals from a stream of fluid carrying droplets, wherein light detected from each wavelength or waveband reports the presence or absence of a different target in individual droplets; (B) combining the at least two separate signals to form a combined signal; (C) processing the combined signal to identify time intervals that correspond to droplets; and (D) determining which droplets contain each different target based on values of each separate signal detected during the identified time intervals.

77. A method of detection for droplet-based assays, comprising: (A) generating at least two signals each representing a respective different waveband of light detected during a series of time intervals from a stream of fluid with droplets; (B) combining values of the at least two signals to form a combined signal; (C) identifying portions of the combined signal that correspond to droplets; and (D) processing values of each of the at least two signals that correspond to the portions identified, to determine which droplets contain each target.

78. A system for detection for droplet-based assays, comprising: (A) one or more detectors configured to detect light from a stream of fluid carrying droplets containing at least two different dyes; and (B) a controller configured to generate separate signals each representing light detected with a different detection configuration during a series of time intervals from a stream of fluid carrying droplets, to combine the at least two separate signals to form a combined signal, and to process the combined signal to identify time intervals that correspond to droplets.

79. A method of detection for droplets, comprising: (A) obtaining droplets including a first dye and a second dye, wherein an emission spectrum of the first dye and an absorption spectrum of the second dye define a waveband of overlap and overlap sufficiently to produce at least half-maximal emission from the first dye if the first dye is excited at a maximal absorption wavelength of the second dye; (B) illuminating the droplets with excitation light capable of exciting the first dye and the second dye, the excitation light being emitted by one or more LEDs and including only a shorter-wavelength segment of the waveband of overlap; and (C) detecting light emitted by the first dye and the second dye, wherein light emitted from the second dye is detected in a wavelength range including only a longer-wavelength segment of the waveband of overlap that is spaced from the shorter-wavelength segment.

80. The method of paragraph 79, wherein the absorption spectrum and the emission spectrum have respective maxima at wavelengths that are within about 20 nm of each other.

81. The method of paragraph 79, wherein the one or more LEDs include a first LED that selectively excites the first dye and a second LED that selectively excites the second dye.

82. The method of paragraph 79, further comprising a step of collecting a first set of data and a second set of data representing light detected selectively from the first dye and the second dye, respectively.

83. The method of paragraph 79, wherein the first dye is FAM dye and the second dye is VIC dye.

84. The method of paragraph 79, wherein the waveband of overlap is defined where the spectra overlap at 20% or more of maximal absorption or emission, and wherein the waveband of overlap extends for least 25 nm.

85. A system for detection in droplet-based assays, comprising: (A) a channel configured to receive droplets including a first dye and a second dye, wherein an emission spectrum of the first dye and an absorption spectrum of the second dye define a waveband of overlap and overlap sufficiently to produce at least half-maximal emission from the first dye if the first dye is excited at a maximal absorption wavelength of the second dye; (B) an illumination assembly including one or more LEDs and configured to illuminate the droplets with excitation light capable of exciting the first and second dyes, the excitation light being emitted by the LEDs and including only a shorter-wavelength segment of the waveband of overlap; and (C) one or more detectors configured to detect light emitted by the first dye and the second dye, wherein the light from the second dye is detected in a wavelength range including only a longer-wavelength segment of the waveband of overlap that is spaced from the shorter-wavelength segment.

86. The system of paragraph 85, wherein the illumination assembly includes one or more filters that define the shorter-wavelength segment.

87. The system of paragraph 85, further comprising a collection assembly including the one or more detectors, were in the collection assembly includes one or more filters that define the longer-wavelength segment.

88. A method of detection for droplets, comprising: (A) generating a beam of light; (B) splitting the beam of light into a main beam and at least one sampling beam; (C) monitoring an intensity of the sampling beam; (D) adjusting an intensity of the beam of light based on one or more measurements from the step of monitoring; (E) illuminating an examination region of a channel with light from the main beam as droplets pass through the examination region; and (F) collecting data representing light detected from the examination region.

89. The method of paragraph 88, wherein the step of generating a beam of light includes a step of filtering light emitted from a light source to change a spectrum of the emitted light, and wherein the step of splitting is performed after the step of filtering.

90. The method of paragraph 88, wherein the step of filtering is performed with a band-pass wavelength filter, a long-pass wavelength filter, a short-pass wavelength filter, or a combination thereof.

91. The method of paragraph 88, wherein the step of generating a beam of light includes a step of combining beams of light emitted from at least two light sources, and wherein the step of combining is performed after the step of filtering.

92. The method of paragraph 88, wherein the step of generating a beam of light includes a step of emitting light with an LED.

93. The method of paragraph 88, wherein the step of generating a beam of light includes a step of combining light from a first light source and a second light source, wherein the step of splitting includes a step of splitting the beam of light into a first sampling beam and a second sampling beam, and wherein the first sampling beam corresponds to the first light source and the second sampling beam corresponds to the second light source.

94. The method of paragraph 93, wherein the step of adjusting keeps substantially constant an intensity of a portion of the main beam corresponding to each light source.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A method of detection for droplets, comprising:
    illuminating an examination region of a channel with first pulses of light and second pulses of light as droplets of an emulsion pass through the examination region, the first pulses being spectrally distinct from and having a same pulse frequency as the second pulses; and
    collecting data representing light detected during illumination of the examination region with the first pulses and the second pulses;
    wherein each droplet is illuminated with a beam of light that is narrower than a diameter of the droplets such that no more than a portion of the droplet is illuminated by the beam of light at any given time.

2. The method of claim 1, wherein light for the first pulses is produced by a first light source, and wherein light for the second pulses is produced by a second light source.

3. The method of claim 1, wherein the first pulses, the second pulses, or both the first and second pulses are produced by at least one continuous light beam that is transmitted intermittently to the examination region.

4. The method of claim 1, wherein overlapping volumes of the examination region are illuminated by the first pulses and the second pulses.

5. The method of claim 1, further comprising a step of detecting light from overlapping volumes of the examination region during the first pulses and the second pulses.

6. The method of claim 1, wherein each droplet is illuminated with at least one first pulse and at least one second pulse.

7. The method of claim 1, wherein the data represents light detected with a same detector during illumination of the examination region with the first pulses and the second pulses.

8. The method of claim 1, wherein the step of illuminating includes a step of intersecting the channel with a beam of light having a cross section that is elongated transversely to a long axis defined by the channel.

9. A system for detection in droplet-based assays, comprising:
    a channel;
    an illumination assembly including a light source and a slit and configured to produce a beam of light that illuminates an examination region of the channel as droplets pass through such region;
    a detector configured to detect light received from the examination region; and
    a controller that collects data representing light detected by the detector,
    wherein light from the light source is shaped by the slit such that the beam of light is elongated in cross section where the beam intersects the channel; and
    wherein the beam of light at the examination region is narrower than the diameter of each droplet such that no more than a portion of the droplet is illuminated by the beam of light at any given time.

10. The system of claim 9, wherein the beam of light is elongated in cross section in a direction transverse to a long axis defined by the channel.

11. The system of claim 9, wherein a cross section of the beam, at a position halfway across the channel, extends outside opposing surfaces of the channel.

12. The system of claim 9, wherein the beam of light has a dimension measured parallel to a long axis of the channel where the channel and the beam intersect, and wherein the dimension is less than a diameter of the channel.

13. A method of detection for droplets, comprising:
    illuminating an examination region of a channel with first pulses of light and second pulses of light as droplets of an emulsion pass through the examination region, the first pulses being spectrally distinct from and having a same pulse frequency as the second pulses; and
    collecting data representing light detected during illumination of the examination region with the first pulses and the second pulses.

14. The method of claim 13, wherein the examination region is illuminated with a second pulse between each successive pair of first pulses and with a first pulse between each successive pair of second pulses.

15. The method of claim 13, wherein a same detector detects light representing the first pulses and the second pulses.

16. The method of claim 13, wherein a first detector detects light representing the first pulses and a second detector detects light representing the second pulses.

17. The method of claim 13, wherein the step of collecting data includes a step of synchronizing generation of first signals with the first pulses and second signals with the second pulses.

18. The method of claim 17, wherein the step of synchronizing includes a step of periodically gating an analog signal from a detector before the analog signal is converted to digital form.

19. The method of claim 17, wherein the first signals represent light detected by a first detector and the second signals represent light detected by a second detector.

20. The method of claim 19, wherein the step of synchronizing includes a step of optically gating light incident on each detector.

21. The method of claim 19, wherein the step of synchronizing includes a step of adjusting a gain of each detector.

22. The method of claim 13, wherein light for the first pulses is produced by a first light source, and wherein light for the second pulses is produced by a second light source.

* * * * *